United States Patent
Coenen et al.

(10) Patent No.: US 11,684,522 B2
(45) Date of Patent: Jun. 27, 2023

(54) ELASTIC LAMINATES WITH CURVED ELASTICS AND METHODS FOR MANUFACTURING

(71) Applicant: Kimberly-Clark Worldwide, Inc., Neenah, WI (US)

(72) Inventors: Joseph D. Coenen, Kaukauna, WI (US); Ross T. Kaufman, Appleton, WI (US); Kelly D. Farmer, Neenah, WI (US); Jerry L. Hameister, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 424 days.

(21) Appl. No.: 16/652,724

(22) PCT Filed: Oct. 31, 2018

(86) PCT No.: PCT/US2018/058342
§ 371 (c)(1),
(2) Date: Apr. 1, 2020

(87) PCT Pub. No.: WO2019/089682
PCT Pub. Date: May 9, 2019

(65) Prior Publication Data
US 2020/0237576 A1 Jul. 30, 2020

Related U.S. Application Data

(60) Provisional application No. 62/579,546, filed on Oct. 31, 2017.

(51) Int. Cl.
*B32B 37/14* (2006.01)
*A61F 13/49* (2006.01)
*A61F 13/15* (2006.01)

(52) U.S. Cl.
CPC .... *A61F 13/4902* (2013.01); *A61F 13/15593* (2013.01); *A61F 2013/49025* (2013.01);
(Continued)

(58) Field of Classification Search
CPC ............ B32B 2555/02; B32B 2307/51; B32B 37/144; A61F 2013/49025; A61F 13/15593; A61F 13/4902
See application file for complete search history.

(56) References Cited

U.S. PATENT DOCUMENTS

| | | | |
|---|---|---|---|
| 5,275,676 A | 1/1994 | Rooyakkers et al. | |
| 5,525,175 A | 6/1996 | Blenke et al. | |

(Continued)

FOREIGN PATENT DOCUMENTS

| | | |
|---|---|---|
| CN | 101230519 A | 7/2008 |
| CN | 104203177 A | 12/2014 |

(Continued)

OTHER PUBLICATIONS

DiaperFetch, "Adult Diaper & Briefs—Tena Adult Briefs & Other Premium Brands", https://www.diaperfetch.com/shop/tena-adult-diaper-briefs/, Year: 2015.

(Continued)

*Primary Examiner* — Vishal I Patel
(74) *Attorney, Agent, or Firm* — Kimberly-Clark Worldwide, Inc.

(57) ABSTRACT

Elasticated materials and articles comprising elasticated materials are disclosed. A method may comprise advancing first and second substrate materials and a stretched elastomeric strand in the machine direction. The method may further comprise advancing the first and the second substrate materials with the elastomeric strand positioned therebetween to a bonding apparatus. The bonding apparatus may comprise first and second elements forming a bonding nip.

(Continued)

The method may further comprise oscillating the strand in a cross-machine direction and advancing the first and second substrate materials, and the strand, through the bonding nip and bonding the first and second substrate materials together with at least first and second bonds. The first and second bonds may be disposed on opposite sides of the strand and spaced apart a distance less than its un-tensioned diameter, and the first and second bonds may be located along an arcuate portion of the strand.

7 Claims, 19 Drawing Sheets

(52) U.S. Cl.
CPC ......... *B32B 37/144* (2013.01); *B32B 2307/51* (2013.01); *B32B 2555/02* (2013.01)

(56) References Cited

U.S. PATENT DOCUMENTS

| | | | |
|---|---|---|---|
| D446,303 S | 8/2001 | Glaug et al. | |
| 6,291,039 B1 | 9/2001 | Combe et al. | |
| 6,635,041 B1 * | 10/2003 | Popp | A61F 13/15593 604/385.27 |
| 7,297,139 B2 | 11/2007 | Price et al. | |
| D577,817 S | 9/2008 | Rinaldi et al. | |
| 7,582,348 B2 | 9/2009 | Ando et al. | |
| 7,867,213 B2 | 1/2011 | Bandorf et al. | |
| D645,144 S | 9/2011 | Mason et al. | |
| 8,261,802 B2 | 9/2012 | Aono | |
| 8,647,319 B2 | 2/2014 | Een et al. | |
| 9,011,404 B2 | 4/2015 | Kobayashi et al. | |
| D762,849 S | 8/2016 | Davenport | |
| D780,911 S | 3/2017 | Fites et al. | |
| D789,525 S | 6/2017 | Fites et al. | |
| 2002/0019616 A1 | 2/2002 | Thomas | |
| 2003/0124331 A1 | 7/2003 | Morell et al. | |
| 2003/0144643 A1 | 7/2003 | Jarpenberg et al. | |
| 2006/0069373 A1 | 3/2006 | Schlinz et al. | |
| 2006/0228969 A1 | 10/2006 | Erdman | |
| 2009/0047855 A1 | 2/2009 | Seth et al. | |
| 2009/0275908 A1 | 11/2009 | Song | |
| 2010/0076394 A1 | 3/2010 | Hayase et al. | |
| 2012/0095429 A1 | 4/2012 | Kobayashi et al. | |
| 2013/0281957 A1 | 10/2013 | Fritz et al. | |
| 2015/0328056 A1 | 11/2015 | Een et al. | |
| 2016/0106601 A1 | 4/2016 | Kobayashi et al. | |
| 2016/0159062 A1 | 6/2016 | Sablone | |
| 2016/0228305 A1 | 8/2016 | Gualtieri et al. | |
| 2016/0288407 A1 | 10/2016 | Ehlert et al. | |
| 2016/0331600 A1 | 11/2016 | Polidori et al. | |
| 2017/0000660 A1 | 1/2017 | Wade et al. | |

FOREIGN PATENT DOCUMENTS

| | | | |
|---|---|---|---|
| CN | 104203180 A | 12/2014 | |
| EP | 1529623 A2 | 5/2005 | |
| JP | 2009118986 A | 6/2009 | |
| JP | 4884272 B2 | 2/2012 | |
| JP | 2013126527 A | 6/2013 | |
| JP | 2017064227 A | 4/2017 | |
| WO | 9855292 A1 | 12/1998 | |
| WO | 08041639 A1 | 4/2008 | |
| WO | 15042351 A1 | 3/2015 | |
| WO | 15146704 A1 | 10/2015 | |
| WO | 16121982 A1 | 8/2016 | |
| WO | WO-2016160752 A1 * | 10/2016 | ............ B29C 65/08 |

OTHER PUBLICATIONS

Co-Pending U.S. Appl. No. 16/652,720, filed Apr. 1, 2020, by Csida et al. for "Elastic Laminates with Curved Elastics and Methods for Manufacturing."

* cited by examiner

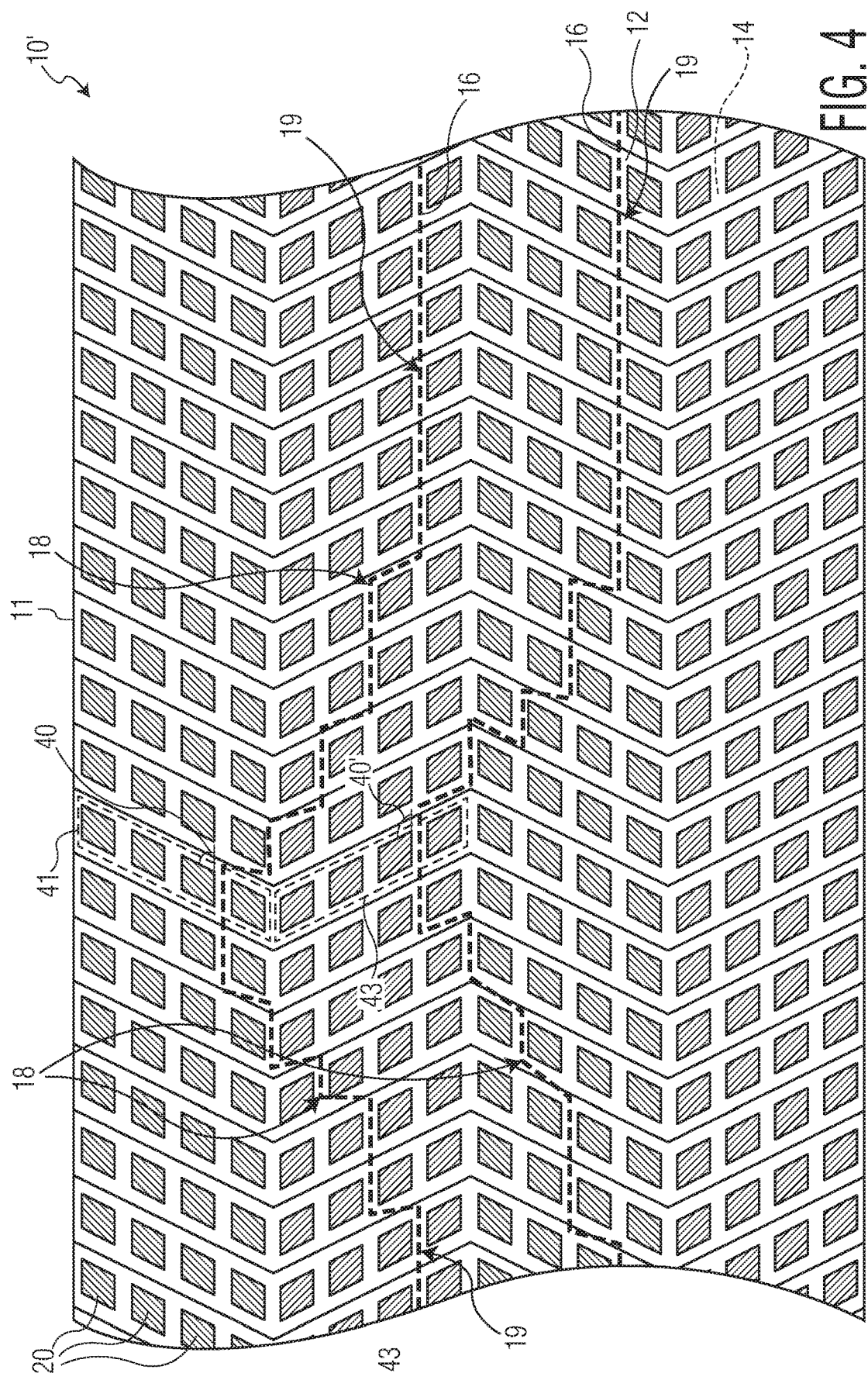

ELASTIC LAMINATES WITH CURVED ELASTICS AND METHODS FOR MANUFACTURING

PRIORITY CLAIM

The present application claims priority to U.S. Provisional Application No. 62/579,546, entitled "Elastic Laminates With Curved Elastics And Methods For Manufacturing" and filed on Oct. 31, 2017, and to U.S. Provisional Application No. 62/579,494, entitled "Elastic Laminates With Curved Elastics And Methods For Manufacturing" and filed on Oct. 31, 2017, the contents of which are hereby incorporated by reference in a manner consistent with the present application.

TECHNICAL FIELD

The present disclosure relates to elasticated materials, and more specifically elasticated materials that have curved elastomeric strands.

BACKGROUND OF THE DISCLOSURE

Elasticated materials are used in many different applications, including within various clothing garments and absorbent articles. Such elasticated materials may be used as part of waistbands, leg cuffs, barrier cuffs, or in other components of clothing garments and absorbent articles to provide beneficial fit characteristics, help prevent leakage of bodily exudates, or impart other benefits.

Many current clothing garments and absorbent articles include elasticated materials which comprise elastomeric strands positioned between layers of material and affixed to the layers of material with adhesive. Some prior art elasticated materials have attempted to remove the adhesive in favor of affixing the elastomeric strands to the layers of material with the use of discrete individual bonds. These prior art materials position the bonds across the elastomeric strands a distance less than the un-tensioned diameter of the elastomeric strands. Some example prior art materials can be seen in U.S. Pat. No. 6,291,039 to Cera France Compagnie d'Equipment Robotique Appliquee, titled "Ruffling Slide and Method for Making Same". This particular structural configuration holds the elastomeric strands in place within the elasticated material between the bonds. These adhesiveless elasticated materials have a cost advantage as they do not require adhesive to affix the elastomeric strands within the elasticated material. Forming elasticated materials in this fashion with curved elastomeric strands has been found to be problematic, as curving the elastomeric strands during manufacture of such elasticated materials can cause the bonds to be formed through the elastomeric strands, thereby breaking or otherwise damaging the elastomeric strands. Accordingly, elasticated materials and processes to form elasticated materials which do not include adhesive and which include curved elastomeric strands and which do not suffer from strand breakage are desired.

SUMMARY OF THE DISCLOSURE

The present disclosure relates to elasticated materials, and more specifically elasticated materials that have curved elastomeric strands. In general, the elasticated materials of the present disclosure are constructed without adhesive and include elastomeric strands which form a generally arcuate or curved shape. Forming elasticated materials without the use of adhesive provides a great cost advantage in terms of reduction in the adhesive employed in an absorbent article garment, in addition to the associated machinery required for adhesive application. The lack of adhesive also has advantages relating to product benefits such as increased softness and unique visible patterning due to the discrete bonds. The arcuate or curved elastomeric strands may provide a better fit control.

In one embodiment, a method for forming an elasticated material may comprise advancing a first continuous substrate material having an upper surface and a lower surface in a machine direction, advancing a second continuous substrate material having an upper surface and a lower surface in the machine direction, and advancing an elastomeric strand in a stretched state in the machine direction, wherein the elastomeric strand is positioned between the lower surface of the first continuous substrate material and the upper surface of the second continuous substrate material. The method may further comprise advancing the first continuous substrate material and the second continuous substrate material with the elastomeric strand positioned therebetween to a bonding apparatus. The bonding apparatus may comprise a first bonding element and a second bonding element disposed proximate the first bonding element and forming a bonding nip with the first bonding element. The method may also comprise oscillating the elastomeric strand in a cross-machine direction, advancing the first continuous substrate material, the second continuous substrate material, and the elastomeric strand through the bonding nip and bonding the first continuous substrate material to the second continuous substrate material with the elastomeric strand disposed therebetween with at least a first bond and a second bond. The first bond and the second bond may be disposed on opposite sides of the elastomeric strand and spaced apart a distance less than an un-tensioned diameter of the elastomeric strand and may be located along a portion of the elastomeric strand which extends in an arcuate manner.

In another embodiment, a method for forming an elasticated material may comprise advancing a first continuous substrate material having an upper surface and a lower surface in a machine direction, advancing a second continuous substrate material having an upper surface and a lower surface in the machine direction, advancing an elastomeric strand in a stretched state in the machine direction, wherein the elastomeric strand is positioned between the lower surface of the first continuous substrate material and the upper surface of the second continuous substrate material, and advancing the first continuous substrate material and the second continuous substrate material with the elastomeric strand positioned therebetween to a bonding apparatus. The bonding apparatus may comprise a first bonding element, a second bonding element disposed proximate the first bonding element and forming a bonding nip with the first bonding element, and a guide element disposed proximate the second bonding element and forming a guide nip with the second bonding element. The method may further comprise oscillating the elastomeric strand in a cross-machine direction, advancing the second continuous substrate and the elastomeric strand through the guide nip so that the second continuous substrate and the elastomeric contact the second bonding element prior to the bonding nip, and advancing the first continuous substrate material, the second continuous substrate material, and the elastomeric strand through the bonding nip and bonding the first continuous substrate material to the second continuous substrate material with the elastomeric strand disposed therebetween with at least a first bond and a second bond. The first bond and the second bond may be disposed on opposite sides of the elastomeric strand and spaced apart a distance less than an un-tensioned diameter of the elastomeric strand and located along a portion of the elastomeric strand which extends in an arcuate manner.

In a further embodiment, an elasticated material may comprise a first substrate layer, a second substrate layer, an elastomeric strand disposed between the first substrate layer and the second substrate layer, and a plurality of bonds bonding the first substrate layer to the second substrate layer. The elastomeric strand may comprise at least one straight portion and at least one arcuate portion. The plurality of bonds may comprise a first bond and a second bond, and the first bond and the second bond may be disposed on opposite sides of the elastomeric strand and spaced apart a distance less than an un-tensioned diameter of the elastomeric strand and located along an arcuate portion of the elastomeric strand.

The above summary of the present disclosure is not intended to describe each embodiment or every implementation of the present disclosure. Advantages and attainments, together with a more complete understanding of the disclosure, will become apparent and appreciated by referring to the following detailed description and claims taken in conjunction with the accompanying drawings.

BRIEF DESCRIPTION OF DRAWINGS

The disclosure may be more completely understood in consideration of the following detailed description of various embodiments in connection with the accompanying drawings, in which:

FIG. 4 is a plan view of another elasticated material according to aspects of the present disclosure;

Figure 1:
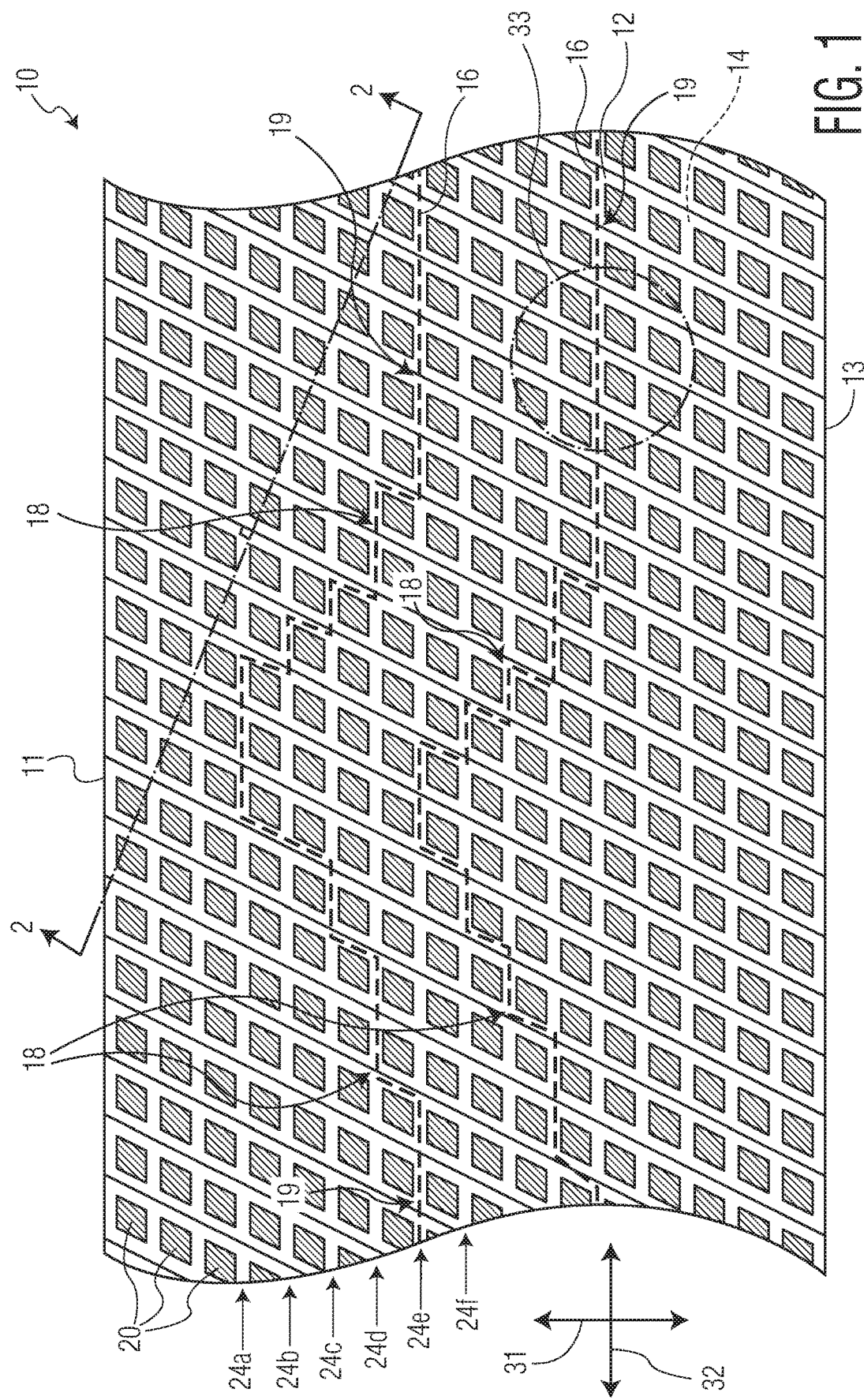
FIG. 1 is a plan view of an elasticated material according to aspects of the present disclosure.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the scope of the disclosure.

DETAILED DESCRIPTION OF THE DISCLOSURE

The present disclosure is generally directed toward elasticated materials and processes for forming elasticated materials having arcuate or curved elastomeric strands. In general, the elasticated materials may not require adhesive to affix the elastomeric strands within the material. Although, it should be understood that in some embodiments the elasticated materials disclosed herein may benefit from applications of adhesive as well. For instance, the elasticated materials may employ laminating adhesive to ensure consistent contact and minimal slipping between the materials of the elasticated materials. The present disclosure details a number of different material structures that can be formed by the described processes using different bonding patterns to affix elastomeric strands in an arcuate or curved shape within an elasticated material.

Each example is provided by way of explanation and is not meant as a limitation. For example, features illustrated or described as part of one embodiment or figure can be used on another embodiment or figure to yield yet another embodiment. It is intended that the present disclosure include such modifications and variations.

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, adult diapers and pants, medical garments, surgical pads and bandages, other personal care or health care garments, and the like without departing from the scope of the present disclosure.

The term "bonded", "attached" or "coupled" refers herein to the joining, adhering, connecting, attaching, or the like, of two elements. Two elements will be considered bonded, attached or coupled together when they are joined, adhered, connected, attached, or the like, directly to one another or indirectly to one another, such as when each is directly bonded to intermediate elements. The bonding, attaching or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer liquids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, hydroentangling processes, etc.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "elasticated" when used herein to describe a material or a portion of an article means that the material or article it is made of an inelastic sheet material coupled to elastomeric material, e.g. one or more elastomeric bands or strands, such that the material or article exhibits elastic properties.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Elasticated Material:

FIG. 1 is a top plan view depicting a portion of exemplary elasticated material 10. The elasticated material 10 generally extends in both the longitudinal direction 31, between a top sheet edge 11 and a bottom sheet edge 13, and the lateral direction 32. The elasticated material 10 may generally comprise a first layer of material 12, a second layer of material 14, elastomeric strands 16, and bonds 20. As will be described in more detail below, at least some of the bonds 20 may be positioned on opposite sides of the elastomeric strands 16 in such a manner that the bonds 20 affix, or "entrap", portions of the elastomeric strands 16 in place within the elasticated material 10.

Figure 3A:
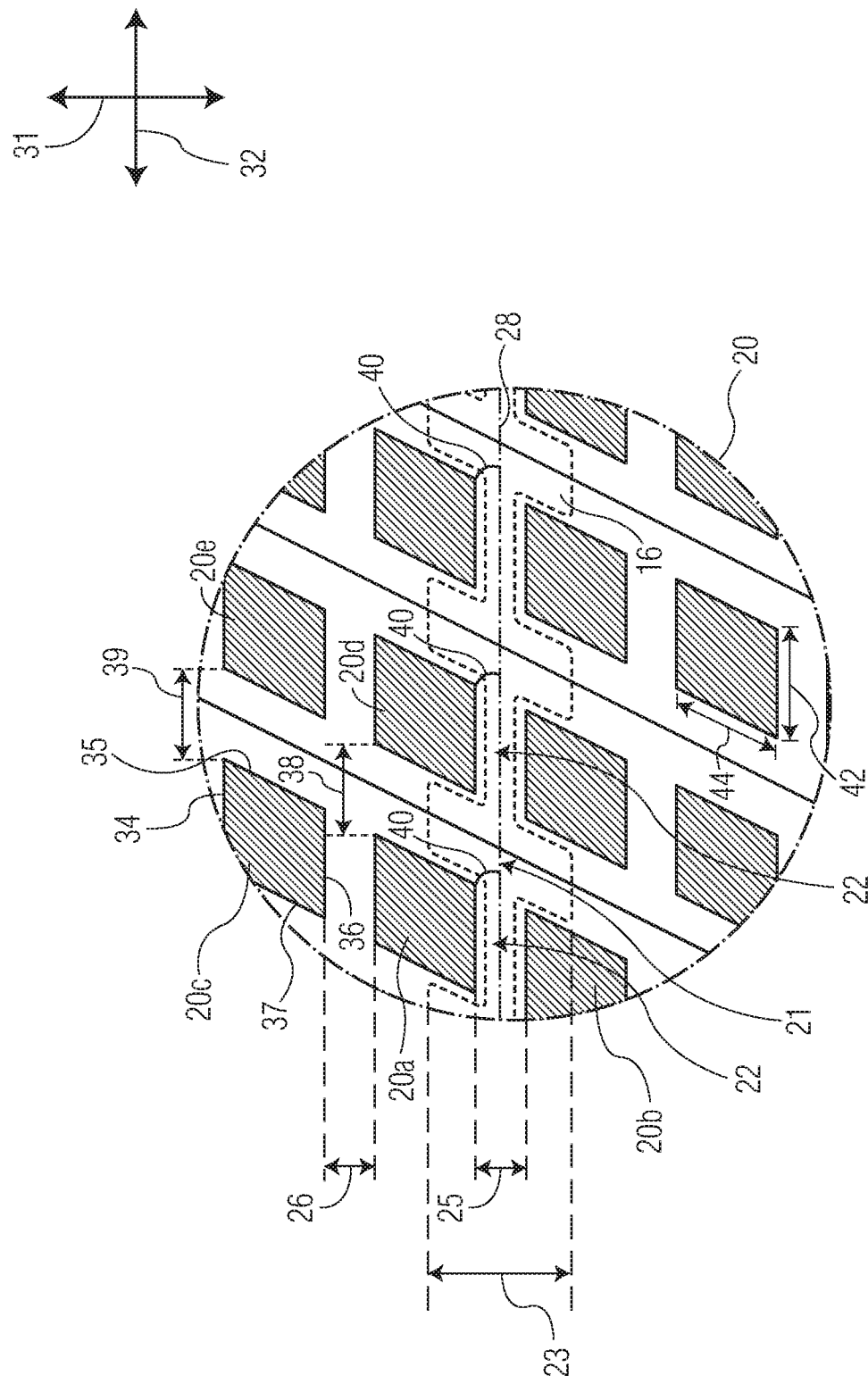
FIGS. 3A-3C are close-up views of the elasticated material of FIG. 1 depicting different aspects of the present disclosure.

FIG. 3A depicts a close-up view of circle 33 of FIG. 1, detailing the bonds 20 and one of the elastomeric strands 16 of the elasticated material 10 in more detail, showing the entrapping of the depicted elastomeric strand 16. Specifically, FIG. 3A depicts the outer edges of the elastomeric strand 16 with dashed lines as the strand 16 passes between pairs of bonds 20, such as bonds 20a and 20b which entrap the strand 16. As can be seen, the elastomeric strand 16 in FIG. 3A may have non-entrapped portions 21 and entrapped portions 22, which alternate along the lateral length of the elastomeric strand 16.

In order to form a material such as the elasticated material 10, with elastomeric strands 16 entrapped within between the layers of material 12, 14, the elastomeric strands 16 may be stretched before or as the elastomeric strands 16 are positioned between the first layer of material 12 and the second layer of material 14. The elastomeric strands 16 may have an un-tensioned outer diameter, and the outer diameter of the elastomeric strands 16 may decrease as the strands 16 are stretched. Accordingly, before or at the time the strands 16 are placed between the first layer of material 12 and the second layer of material 14, the elastomeric strands 16 may have an outer diameter that is less than their un-tensioned outer diameter. Then, at least a pair of the bonds 20 of the material 10, for example bonds 20a, 20b in FIG. 3A, may be placed on opposite sides of the stretched elastomeric strand 16 and spaced apart longitudinally across the strand 16 a longitudinal distance 25. In some embodiments, the longitudinal distance 25 may be approximately equal to the outer diameter of the strand 16 at the time the bond pair 20a, 20b is formed. In other embodiments, the longitudinal distance 25 may be greater than the outer diameter of the strand 16 at the time the bond pair 20a, 20b is formed, but less than the outer diameter of the un-tensioned diameter of the strand 16.

As the elastomeric strands 16 of the elasticated material such as material 10 are allowed to relax, the outer diameter of the elastomeric strands 16 generally increases back toward their un-tensioned outer diameter. However, as can be seen in FIG. 3A, this expansion is inhibited in the entrapped portions 22 of the elastomeric strand 16 by the bonds 20 which are positioned across the strands 16 a longitudinal distance less than the un-tensioned diameter of the strands 16, such as bond pairs 20a, 20b and 20d, 20e and the like. As the elastomeric strand 16 of FIG. 3A relaxes and contracts from a stretched state, the non-entrapped portions 21 of the elastomeric strand 16 expands in the longitudinal direction 31 (e.g. the outer diameter of the elastomeric strand 16 increases), resulting in the structure as seen in FIG. 3A with the elastomeric strand 16 shown having expanded outer diameter 23 in the non-entrapped portions 21. The entrapped portions 22 result in the elastomeric strand 16 being affixed in place within the material 10.

Figure 2:
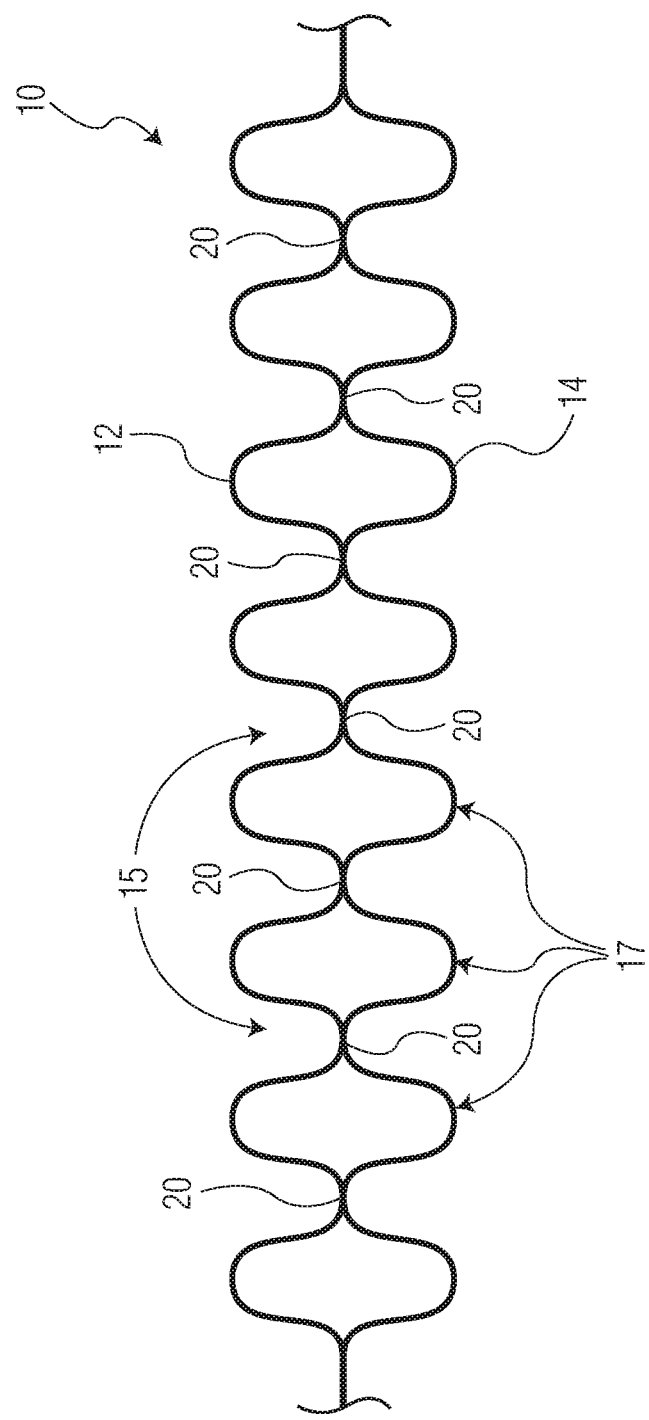
FIG. 2 is a cross-section view of the elasticated material of FIG. 1 as viewed along line 2-2.

The relaxation of the elastomeric strands 16 causes contraction of the strands 16 between entrapped portions 22. This contraction causes corresponding valleys 15 and ridges 17 to form within the elasticated material 10. The structure of the elasticated material 10, including the valleys 15 and the ridges 17, may be seen more clearly in FIG. 2, which is a cross-section of the elasticated material 10 of FIG. 1, as viewed along line 2-2 which extends perpendicular to the ridges 15 and valleys 17 of the elasticated material 10.

In some embodiments, the expanded diameter 23 of the elastomeric strand 16 may be the same as the un-tensioned diameter of the elastomeric strand 16, but in other embodiments this may not be the case. For example, the specific configuration of the type of elastomeric strand 16, the amount of elongation of the elastomeric strand 16 in the forming process, and the location of the bonds 20 in relation to the elongated elastomeric strand 16, both in the longitudinal distance 25 between bonds 20 that span the elastomeric strand 16 and/or the lateral distance between bonds 20, may prevent the diameter of the elastomeric strand 16 from expanding in the non-entrapped portions 21 all the way back to the un-tensioned diameter of the strand 16. Accordingly, in some embodiments the expanded diameter 23 in the non-entrapped portions 21 of at least some of the elastomeric strands 16 of the material 10 may still be less than the un-tensioned diameter of the elastomeric strands 16.

Accordingly, in the above manner, the elastomeric strands 16 may be entrapped within the elasticated material 10. Additionally, as can be seen in FIG. 1, in some embodiments the elasticated material 10 may include entrapped elastomeric strands 16 extending through the material 10 in a generally arcuate manner. Having elastomeric strands 16 extend through the material 10 in a generally arcuate manner may provide desired stretch properties in the material 10. As one example, the arcing elastomeric strands 16 may allow for better fit of an article utilizing the material 10.

As used herein, the term "arcuate" or "generally arcuate" encompasses the general shape the portions of the elastomeric strands 16 form where the strands 16 extend in both the lateral and longitudinal directions 31, 32 through the elasticated materials of the present disclosure. For instance, as shown in FIG. 1, the elastomeric strands 16 comprise generally arcuate portions 18. In some embodiments, the elasticated materials of the present disclosure may comprise straight portions 19. Straight portions may be defined as portions of the strands 16 which extend in substantially a single direction (generally the lateral direction 31) for an appreciable distance without extending in a separate, second direction (such as the longitudinal direction 32)—such as more than about 5 mm or more than about 10 mm or more than about 15 mm.

In some embodiments of elasticated materials contemplated by the present disclosure, the one or more elastomeric strands 16 may have a generally continuous arcuate shape where the strands 16 do not comprise straight portions 19. In other contemplated embodiments, the strands 16 may alternate between arcuate portions 18 and straight portions 19. One such embodiment, shown in FIG. 1, comprises elastomeric strands 16 having straight portions 19, with the arcuate portions 18 disposed between the straight portions 19.

In general, longitudinally adjacent bonds of the bonds 20 may form bond pairs defining un-bonded channels 24 extending between the bond pairs. In the embodiment of FIG. 1, multiple bond pairs are arranged in laterally extending rows to provide laterally extending un-bonded channels 24. Because the arcuate portions 18 include the strands 16 extending in both the lateral and the longitudinal directions 31, 32, the arcuate portions 18 of the strands 16 may extend through multiple different, longitudinally adjacent un-bonded channels 24. In the example of FIG. 1, the top elastomeric strand left-side arcuate portion 18 extends through un-bonded channel 24e and through longitudinally adjacent un-bonded channel 24d. This arcuate portion 18 further extends through un-bonded channel 24c, which is longitudinally adjacent to the un-bonded channel 24d. This arcuate portion 18 still further extends through un-bonded channels 24b and 24a. The right-hand side arcuate portion 18 extends through un-bonded channel 24a and then back through un-bonded channels 24b, 24c, 24d, and finally back to un-bonded channel 24e. Although called out as separate arcuate portions 18 in the above description, the two described arcuate portions 18 may be considered a single arcuate portion 18, as no straight portion is disposed between the two arcuate portions 18.

In some embodiments where an elastomeric strand 16 comprises multiple straight portions 19 with at least one arcuate portion 18 disposed therebetween, the elastomeric strand 16 may extend through the same, first un-bonded channel 24 along the straight portions 19 located prior to and after the one or more arcuate portions 18. For example, as seen in FIG. 1, the top elastomeric strand 16 is shown extending through un-bonded channel 24e along both straight portions 19. In other embodiments, however, the elastomeric strand 16 may extend through different un-bonded channels 24 along the first and second straight portions 19. For instance, in different embodiments of material 10, the first (left-hand side) straight portion 19 of the strand 16 may extend through un-bonded channel 24e and the second (right-hand side) straight portion 19 may extend through un-bonded channel 24d, or 24f, or any other un-bonded channel of the material 10.

Along arcuate portions 18, there is really no limit to the number of longitudinally adjacent un-bonded channels 24 through which the elastomeric strands 16 may extend. Although the strands 16 shown in FIG. 1 are depicted as extending through only five different un-bonded channels 24 along the arcuate portions 18, this should not be construed as limiting in any fashion. The number of un-bonded channels 24 through which a strand 16 may extend along its arcuate portions 18 may generally be a design decision dictated by the ultimate purpose of the material 10.

Additionally, there is also no lower limit to the number of bond pairs through which an elastomeric strand 16 needs to extend in a given un-bonded channel 24 along its arcuate portions 18. For instance, FIG. 1 shows the elastomeric strands 16 extending through as few as zero bond pairs in a given un-bonded channel, such as channel 24b, and as many as three bond pairs in another un-bonded channel, such as channel 24a. However, these numbers should not be viewed as upper and lower limits. In some preferred embodiments, it may be desirable that the strands 16 extend through at least one, or at least two, or at least three, or at least four, or at least five, bond pairs in each un-bonded channel 24 along arcuate portions 18.

A few contemplated apparatuses and processes for forming the strands 16 with arcuate portions 18 and how to form the bonds 20 with minimal instances of strand breakage will be described in more detail with respect to other of the Figures of the present disclosure.

Web Materials:

In general, the first layer of material 12 and the outer layer of material 14 may be constructed of any materials suitable for use in waistbands, leg cuffs, or any other body-contacting portions, or non-body-contacting portions, of clothing garments and absorbent articles. The layers 12, 14 may be constructed of the same material or different materials. Each of the layers 12, 14 may comprise a single layer, multiple layers, laminates, or the like in different contemplated embodiments. Additionally, the layers 12, 14 may comprise two separate webs of material positioned on opposite sides of the elastomeric strands 16 to form the elasticated material 10, or the layers 12, 14 may comprise a single web of material that is folded over such that a first portion of the web of material is positioned on a first side of the elastomeric strands 16 and a second portion of the web of material is positioned on a second side of the elastomeric strands 16 to form the elasticated material 10.

Exemplary suitable classes of materials for the layers 12, 14, include synthetic fibers (for example, polyethylene or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Additionally, various woven and non-woven fabrics can be used for the layers 12, 14. The layers 12, 14 can comprise woven fabrics, nonwoven fabrics, polymer films, film-fabric laminates or the like, as well as combinations thereof. Examples of nonwoven fabrics can include spunbond fabrics, meltblown fabrics, coform fabrics, carded webs, bonded-carded webs, bicomponent spunbond fabrics, spunlaces, or the like, as well as combinations thereof.

For example, the layers 12, 14 can be composed of a meltblown or spunbond webs of polyolefin fibers. Alternatively, the layers 12, 14 can be bonded-carded webs composed of natural and/or synthetic fibers. The layers 12, 14 can be composed of a substantially hydrophobic materials, and the hydrophobic materials can, optionally, be treated with a surfactant or otherwise processed to impart a desired level of wettability and hydrophilicity. The surfactant can be applied by any conventional means, such as spraying, printing, brush coating or the like. The surfactant can be applied to the entirety of the layers 12, 14 or it can be selectively applied to particular sections of the layers 12, 14. Some specific exemplary materials suitable for the layers 12, 14 include 100% polypropylene bonded-carded webs in the 5-150 gsm range. Other exemplary suitable materials include spunbond polypropylene non-woven webs in the 5-150 gsm range. Still other exemplary materials may have basis weights above 150 gsm.

In an embodiment, the layers 12, 14 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, the layers 12, 14 can be spunbond substrates with a basis weight from about 8 to about 50 gsm. In an embodiment, the layers 12, 14 can be a 12 gsm spunbond-meltblown-spunbond substrate. In another embodiment, the layers 12, 14 can be an 8 gsm spunbond-meltblown-spunbond substrate.

Elastomeric Strands:

Suitable elastomeric materials for the elastomeric strands 16 can include, but are not limited to, spandex elastomeric strands, strands of natural or synthetic rubber, thermoplastic elastomeric materials, or heat activated elastomeric materials. The elastomeric strands 16 can be any elastomeric material capable of being elongated at least about 50 percent, desirably about 350 percent, and capable of recovering to within at least about 250 percent, and desirably about 150 percent of its original length after being elongated about 300 percent. The elastomeric strands 16 can be a spandex elastomeric strand(s) such as, for example, a LYCRA thread commercially available from E. I. DuPont de Nemours and Co. Alternatively, the elastomeric strands 16 can be composed of a thermoplastic elastomer or a natural or a synthetic rubber commercially available from J.P.S. Elastomerics Corp. Alternatively, the elastomeric strands 16 can also be composed of a heat activated elastic material such as PEBAX, commercially available from Atochem, Inc., which can be activated with heat treatment after the elastomeric strands 16 have been disposed within the elasticated material 10 and the bonds 20 have been formed. In at least some embodiments, the elastomeric strands may have diameters that range between about 10 denier to about 1500 denier.

Bonds:

The bonds 20 can be formed through any suitable bonding technique, such as thermal/heat bonding, ultrasonic bonding, pressure bonding, or other known bonding techniques. In general, as will be described in more detail below, the bonds 20 can be formed by use of a pattern component and a smooth component. To form the bonds 20, the layers 12, 14, with the elastomeric strands 16 disposed therebetween, are positioned between the pattern component and the smooth component with appropriate alignment between any features of the pattern component and the elastomeric strands 16. For instance, the elastomeric strands 16 may be positioned between raised protrusions (e.g. bond-forming protrusions) of the pattern component.

For instance, where thermal bonding, pressure bonding, or rotary ultrasonic bonding techniques are used to form the bonds 20, the pattern component and the smooth component may be pattern rolls and smooth rolls, respectively. In such embodiments, the pattern rolls may contain a number of raised portions that protrude from the surface of the pattern rolls. The raised portions may correspond approximately with the shape of the bonds 20 and aligned on the surface of the pattern rolls to produce the longitudinal and latitudinal alignment of the bonds 20 as depicted in the different embodiments of the elasticated materials of the present disclosure. The smooth rolls may generally be solid rolls with smooth outer surfaces.

The heat bonding techniques which may be used to form the bonds 20 may include heating the raised portions of the pattern rolls to between about 70 degrees C. and about 340 degrees C. In general, the level of heating should be less than that which results in melting of the elastomeric strands 16 when the bonds are being formed. While the raised portions are at the appropriate temperature, the pattern roll may be pressed onto the smooth roll, with the layers 12, 14 and the elastomeric strands 16 positioned between the rolls. As some examples, the compressive force used to form the bonds 20 may be between about 500 KPa and about 2,750 KPa, and the layers 12, 14 and the elastomeric strands 16 may pass between the pattern and anvil rolls between about 100 linear meters per minute (mpm) and about 350 (mpm).

The rotary ultrasonic bonding techniques that may be used to form the bonds 20 may use ultrasonic energy in order to form the bonds 20. For instance, as the layers 12, 14 and the elastomeric strands 16 pass between the pattern roll and smooth roll of a rotary ultrasonic bonder, the smooth roll may be vibrated at a frequency of between about 20,000 Hz and about 50,000 Hz, causing internal heating of the layers 12, 14 to such an extent that the layers 12, 14 melt together forming the bonds 20.

The pressure bonding techniques which may be used to form the bonds 20 may be similar to the heat bonding techniques described above, except that no external heat may need to be applied to the raised portions of the pattern roll. However, in order to compensate for the raised portions only being at an ambient temperature, the compressive force applied to the pattern roll and the smooth roll to form the bonds 20 must be greatly increased. In some examples, the compressive force is applied to produce a nip force between about 0.1 KN and about 5 KN, while the layers 12, 14 and the elastomeric strands 16 pass between the pattern roll and the anvil roll at about 15 mpm and 450 mpm.

In non-rotary ultrasonic bonding techniques that may be used to form the bonds 20, the pattern element and the anvil element may be a smooth ultrasonic horn and a patterned anvil. In such embodiments, the anvil component may have the raised portions, while the ultrasonic horn has a generally smooth surface. In some embodiments, the patterned anvil may be a flat plate, while in other embodiments multiple patterned anvils may be spaced around a circumference of a drum and timed to coincide with "strikes" of the ultrasonic horn. In still other embodiments, the patterned anvil may comprise a circular drum with raised protrusions disposed on the surface of the drum. Like with the rotary ultrasonic techniques, the ultrasonic horn may be vibrated at a frequency of between about 20,000 Hz and about 50,000 Hz, as the layers 12, 14 and the elastomeric strands 16 pass between the ultrasonic horn and the patterned anvil. This ultrasonic energy application causes internal heating of the layers 12, 14 to such an extent that the layers 12, 14 melt together forming the bonds 20.

In general, such heat bonding techniques, ultrasonic bonding techniques, and pressure bonding techniques known in the art. It should be understood that the parameters described for the different techniques are only exemplary suitable parameters. The described techniques may be used to form the bonds 20 using such techniques operating with other suitable parameters, as is known in the art. For instance, PCT Patent Application WO 2010/068150, titled "METHOD AND APPARATUS FOR BONDING", which is incorporated herein by reference in its entirety, details methods and apparatus for performing pressure bonding which could be used to form the bonds 20 of the bond patterns described in the present disclosure using many different suitable parameters. It should additionally be understood that the different ways in which the bonds 20 are formed do not appreciably affect the resulting structure of the elasticated material, aside from possibly resulting in different strengths of the bonds 20. However, all of such known techniques are capable of producing bonds which are strong enough to resist the expansion of the elastomeric strands positioned between the bonds 20 without the bonds 20 breaking. Accordingly, the bonds 20 may be formed according to any known bonding technique without departing from the scope of the present disclosure.

In general, the bonds 20 of the elasticated materials 10 of the present disclosure may have any suitable size or shape. However, in at least some embodiments, the bonds 20 may have areas ranging between about 50 square micrometers to about 20 square millimeters, or between about 70 square micrometers to about 10 square millimeters, or between about 250 square micrometers and about 5 square millimeters. Additionally, in some embodiments, the dimension of the bonds 20 in a direction generally parallel to the elastomeric strands 16, e.g. lateral length dimension 42, may be between about two times to about six times greater than the dimension of the bonds 20 that is generally perpendicular to the elastomeric strands 16, e.g. longitudinal height dimension 44. For instance, in the embodiment of FIG. 3A, a lateral length of laterally-extending portions of the bonds 20 (e.g. portions 34, 36) may be between about two times and about six times greater than a longitudinal height of longitudinally-extending portions of the bonds 20 (e.g. portions 35, 37).

Additionally, it should also be understood that the bonds may generally have any longitudinal and/or lateral spacing. For instance, the longitudinal spacing of longitudinally adjacent bonds of the bonds 20, such as 20a and 20b or 20a and 20c of FIG. 3A, may vary depending on whether an elastomeric strand 16 is disposed between the longitudinally adjacent bonds. In some embodiments, the longitudinal spacing between longitudinally adjacent bonds 20a and 20b, as represented by longitudinal distance 25, may be less than the longitudinal spacing between longitudinally adjacent bonds 20a and 20c, represented by longitudinal distance 26, where no elastomeric strand 16 is disposed between bonds 20a, 20c. As an example, the longitudinal distance 25 may be less than the un-tensioned diameter of the elastomeric strand 16, while the longitudinal distance 26 may have any suitable longitudinal spacing including a spacing that is greater than the un-tensioned diameter of any elastomeric strands 16 of the material 10. Such embodiments may allow for a sparser bond pattern in regions of the material 10 where no elastomeric strand 16 is entrapped. Although, in further embodiments, the longitudinal distances 25, 26 may be the same even where an elastomeric strand 16 extends between bonds 20a, 20b, but no elastomeric strand 16 extends between bonds 20a, 20c. In some illustrative examples, the longitudinal distance between longitudinally adjacent bonds 20 between which no elastomeric strand 16 extends (such as bonds 20a, 20c) may vary between about 1 mm and about 500 mm.

The lateral spacing between laterally adjacent bonds of the bonds 20 may be the same throughout the material 10 or may be varied. For instance, in some embodiments the lateral spacing between laterally adjacent bonds 20 which are located adjacent an elastomeric strand 16 (e.g. bonds 20a, 20d), as represented by lateral distance 38, may be less than the lateral spacing between laterally adjacent bonds 20 which are not located adjacent an elastomeric strand 16 (e.g. bonds 20c, 20e), as represented by lateral distance 39. Although, in other embodiments, the lateral distances 38 and 39 may be the same. Additionally, in some embodiments, the lateral spacing between laterally adjacent bonds 20 may vary even between pairs of laterally adjacent bonds 20 which are adjacent an elastomeric strand 16. For instance, when used in a garment or absorbent article, the lateral spacing of bonds 20 may be varied throughout different regions of the garment or article to impart a desired pattern or softness to the material. As some non-limiting examples, the lateral spacing between laterally adjacent bonds of the bonds 20 may vary between about 1 mm and about 500 mm.

FIG. 3A details additional features of bonds 20. For instance, bonds 20 may each include a top portion 34, a bottom portion 36 opposite the top portion 34, a first side portion 35, and a second side portion 37 opposite the first side portion 35. As can be seen, in at least some embodiments, the first side portions 35 of the bonds 20 are angled with respect to the elastomeric strands 16. For instance, the first side portion 35 of bond 20a can be seen forming angle 40 with respect to a lateral axis 28 of the elastomeric strand 16. The angling of the first side portions 35 of the bonds 20 may provide the material 10 with desirable stretch properties and may be beneficial for manufacture of the material 10. In such embodiments, the angle 40 may range anywhere between about 1 degree and about 179 degrees. In some more specific embodiments, the angle 40 may range between about 15 degrees and about 90 degrees, or between about 30 degrees and about 89 degrees, or between about 50 degrees and about 88 degrees. In other embodiments, the angle 40 may range between about 105 degrees and about 180 degrees, or between about 120 degrees and about 179 degrees, or between about 140 degrees and about 178 degrees.

Additionally, as can be seen in FIG. 3A, in at least some embodiments the top portions 34 and the bottoms portions 36 of laterally adjacent bonds of the bonds 20 may generally align. However, in other embodiments, the top portions 34 and bottom portions 36 of laterally adjacent bonds may not generally align, and instead may form a staggered pattern.

Figure 3B:
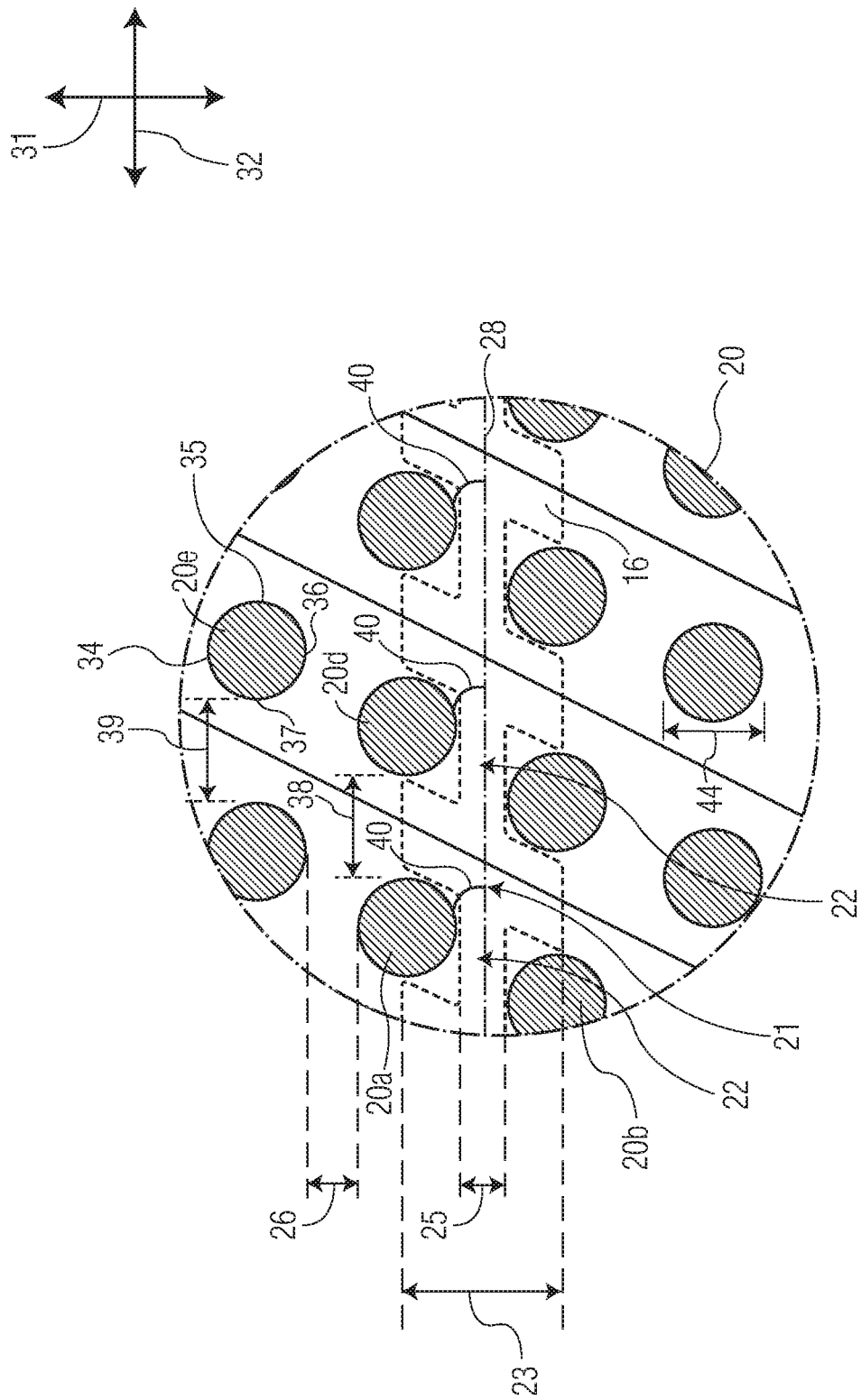
Figure 3C:
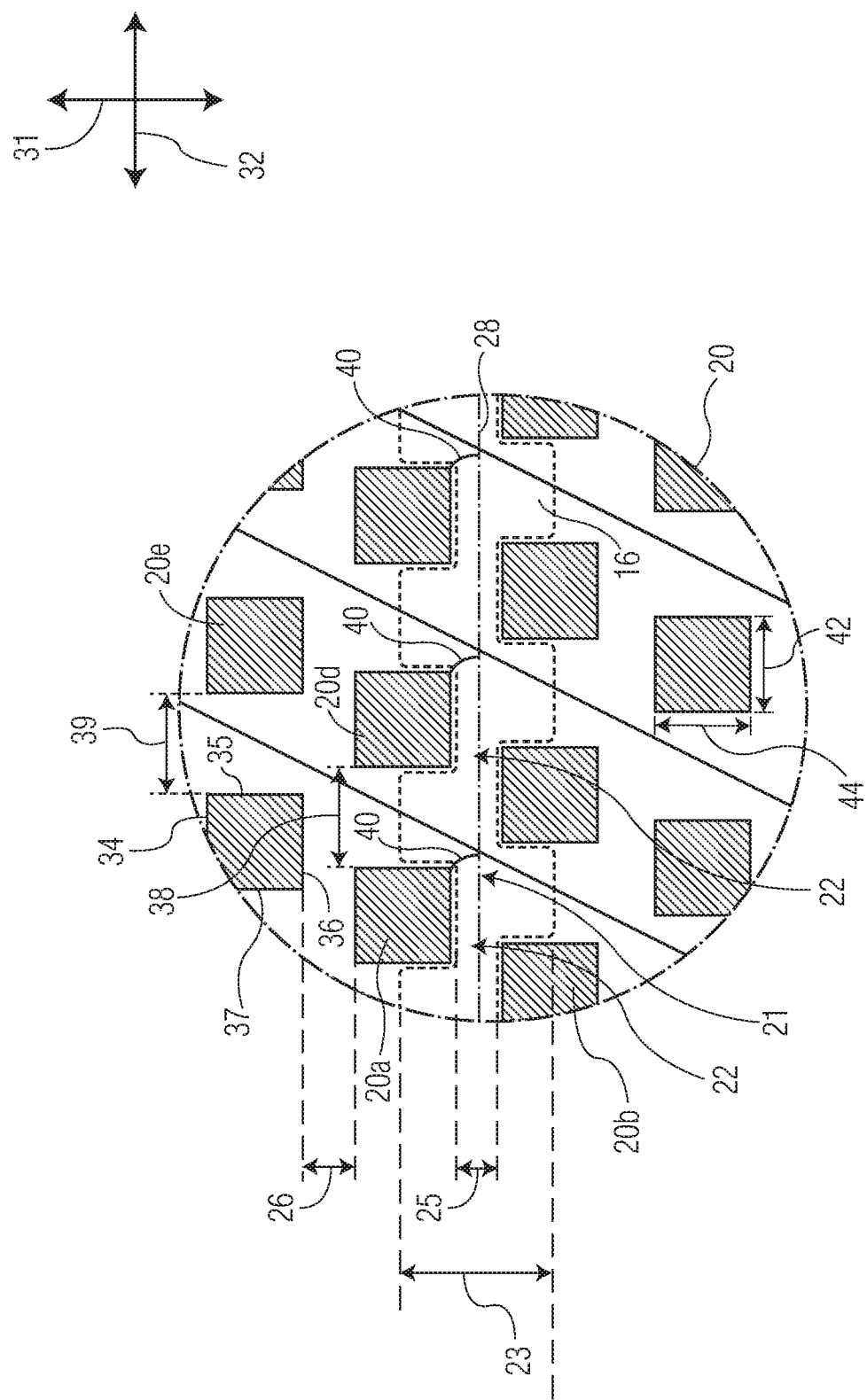

Although shown as generally rectangular, and more specifically as parallelograms, the bonds 20 may be any suitable shape. FIGS. 3B and 3C depict alternatively shaped bonds 20 contemplated by the present disclosure—circles and squares, specifically. In still further contemplated embodiments, however, the bonds 20 may be semi-circular, oval shaped, half-oval shaped, triangular, rectangular, trapezoidal, rhombus-shaped, or the like. In some embodiments, the bonds 20 can have three sides, four sides, five sides, six sides, or any other suitable number of sides.

FIG. 4 depicts an alternative elasticated material 10' of the present disclosure as having a different pattern of the bonds 20 than the pattern of the bonds 20 of material 10 of FIG. 1. As can be seen in FIG. 4, the different bonds 20 may have different angles which they form with respect to the lateral direction 32. Moving from the top sheet edge 11 to the bottom sheet edge 13, bonds 20 within a first grouping of bonds, bond grouping 41, may each form a first angle 40 with respect to the lateral direction 32, while bonds 20 within a second grouping of bonds, bond grouping 43, which are laterally adjacent to the bond grouping 41, may each form a second, different angle 40' with respect to the lateral direction 32. Although each of the bond groupings 41, 43 are shown as comprising four individual bonds 20, it should be understood that there is no real limit to the number of bonds 20 which may be in a bond grouping. The number of bonds 20 in a bond grouping such as groupings 41, 43 may be any suitable number—for example as few as one or as many as one-thousand.

This pattern may be repeated down to the bottom sheet edge 13. In some of these embodiments, the different angles 40 formed by the bonds within the bond groupings 41, 43, may mirror each other about the longitudinal direction 31 such that the angle 40' formed by each of the bonds 20 of the second bond grouping 43 is 180 degrees minus the value of the angle 40 formed by the bonds 20 of the first bond grouping 41 (or vice-versa if the angle 40 formed by the bonds 20 of the first bond grouping 41 is greater than the angle 40' formed by the bonds 20 of the second bond grouping 43). Such a pattern of bonds 20 as shown in FIG. 4 may provide the material 10' with beneficial stretch properties, such as have symmetrical stretch properties.

It should be understood that the patterns of bonds 20 of the materials 10, 10' as shown in FIGS. 1 and 4 should not be construed as limiting the scope of the present disclosure. Rather, any pattern of bonds 20 may be used in combination with this disclosure to produce elasticated materials having elastomeric strands 16 forming generally curved shapes. For example, P.C.T. Application No. PCT/US2017/029845, filed on Apr. 27, 2017 and titled "ELASTICATED MATERIALS WITH DIRECTIONAL STRETCH PROPERTIES", the entirety of which is hereby incorporated by reference, details a number of patterns of bonds, all of which could be employed along with the details of the present disclosure to form elasticated materials having elastomeric strands forming generally curved shapes.

Figure 5:
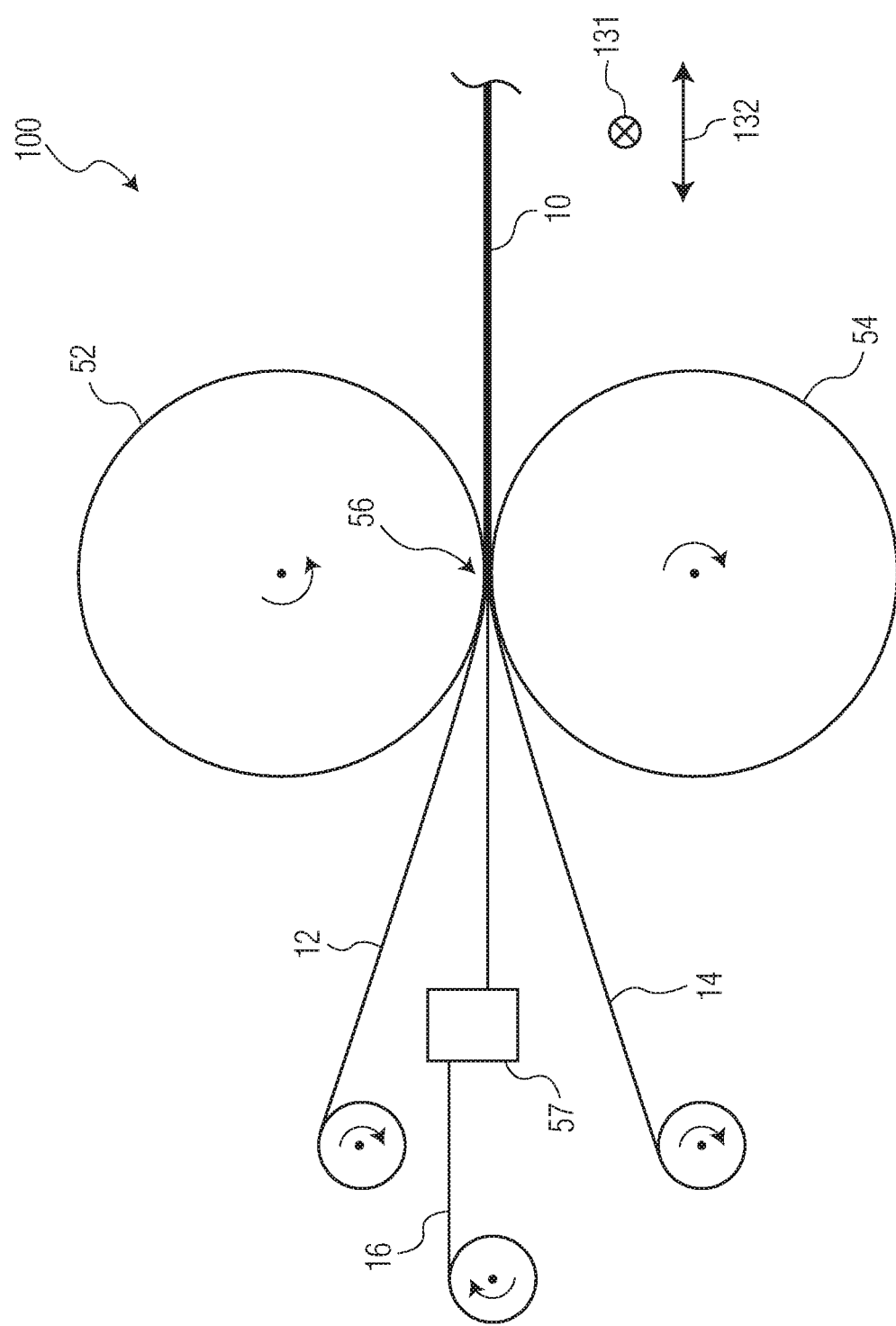
FIG. 5 is a schematic view of a process for forming elasticated materials of the present disclosure.

FIG. 5 is a schematic depiction of an apparatus for practicing an exemplary process 100 for forming the elasticated materials according to the present disclosure. According to the process 100, a first layer of material 12 is fed, in the machine direction 132, between bonding elements 52 and 54 along with a second layer of material 14. One or more elastomeric strands 16 are also fed between the elements 52, 54 and are disposed between the layers 12, 14.

In the embodiment of FIG. 5, the bonding element 52 represents a smooth roll and is shown adjacent bonding element 54 forming a bonding nip 56. The bonding element 54 represents a pattern roll which comprises raised protrusions forming a pattern corresponding to a desired bond pattern of the formed elasticated material 10. The layers of material 12, 14 and the elastomeric strands 16 may come together at least at bonding nip 56, where the first layer of material 12 is bonded to the second layer of material 14, with the elastomeric strands 16 disposed therebetween, by the bonding elements 52, 54. The type of bonding employed by the bonding elements 52, 54 may be any of the bonding types described previously in relation to the details about the bonds 20 and forming the bonds 20, or any other suitable type of bonding. Of course, in embodiments where the bonds 20 are formed according to different bonding modalities, the bonding elements 52, 54 may not be rolls where necessitated by the specific bonding modality. For example, the bonding element 52 may comprise a smooth non-rotary ultrasonic element while the bonding element 54 comprises a patterned rotary anvil element where a non-rotary ultrasonic bonding modality is employed.

According to the process 100, one or more of the elastomeric strands 16 may further be oscillated across the face of the bonding element 54, in the cross-machine direction 131, by oscillating device 57. Oscillating device 57 may comprise any conventional device commonly used to oscillated elastomeric strands. This oscillation of the one or more elastomeric strands 16 forms the one or more arcuate portions 18 of the one or more strands 16, with the generally arcuate shape of the portions 18 held in place once the material 12 is bonded to the material 14.

One challenge in forming the generally arcuate or curved shape of the one or more elastomeric strands 16 is that the oscillation of the one or more elastomeric strands 16 causes the one or more elastomeric strands 16 to cross over the raised protrusions of the bonding element 54. If any of the one or more elastomeric strands 16 crosses over a raised protrusion of the bonding element 54 at the nip 56, the raised protrusion may compress the one or more elastomeric strands 16 against the bonding element 52 and break or otherwise damage the one or more elastomeric strands 16. In this manner, forming elasticated materials with elastomeric strands having a generally curved shaped is more difficult than forming elasticated materials with elastomeric strands extending in a generally straight manner because, in the latter materials, the elastomeric strands may be more easily aligned between the raised protrusions prior to the bonding nip 56.

One option for decreasing the frequency of breakage or damage to the elastomeric strands 16 within the process 100 is to use bond patterns which form entrapping regions and non-entrapping regions within the elasticated material. In such embodiments, the oscillator 57 may be configured to oscillate the one or more elastomeric strands 16 so as to align the arcuate portions 18 within the portions of the bonding element 54 comprising raised protrusions which have a pattern forming the non-entrapping regions of the elasticated material. The non-entrapping regions may generally have a lower average bonded area than the average bonded area of the entrapping regions. The lower average bonded area means less opportunity for the elastomeric strands to align with the raised protrusions of the bonding element 54 as the bonds 20 are formed during the bonding process 100. Accordingly, in such embodiments, there is less opportunity for breakage of the strands 16 during formation of the bonds 20.

The elasticated materials 10 and 10' of FIGS. 1-4 depict embodiments where the one or more elastomeric strands 16 have arcuate portions 18, and where the bonds 20 form un-bonded channels 24 which entrap the one or more elastomeric strands 16 both along their arcuate portions 18 and along their straight portions 19. That is, the bonds 20 disposed along the arcuate portions 18 (and the straight portions 19) of the strands 16 are disposed such that pairs of the bonds 20 disposed on opposite sides of the strands 16 along their arcuate portions 18 are spaced apart a distance less than an un-tensioned diameter of the elastomeric strands 16. As mentioned, such materials 10, 10' can be somewhat difficult to manufacture, particularly at high speeds, due to breakage of the strands 16 during manufacture.

FIGS. 6-12 depict other contemplated embodiments of the present disclosure which comprise elasticated materials having both non-entrapping regions 118 and entrapping regions 119, with the non-entrapping regions 118 aligned with the arcuate portions 18 of the one or more elastomeric strands 16. Such embodiments may be relatively easier to manufacture and/or result in less breakage of the strands 16 during manufacture due to the lower average bonded area within the non-entrapping regions 118, as will be described in more detail below with respect to the different embodiments. The lower average bonded area refers to the fact that, within a given section within a non-entrapping region 118, the ratio of the total amount of bonded area (e.g. bonding the first layer 12 to the second layer 14) to the total area of the given section will be less than the ratio of the total amount of bonded area to the total area within a same-sized section disposed within an entrapping region 119.

Figure 6:
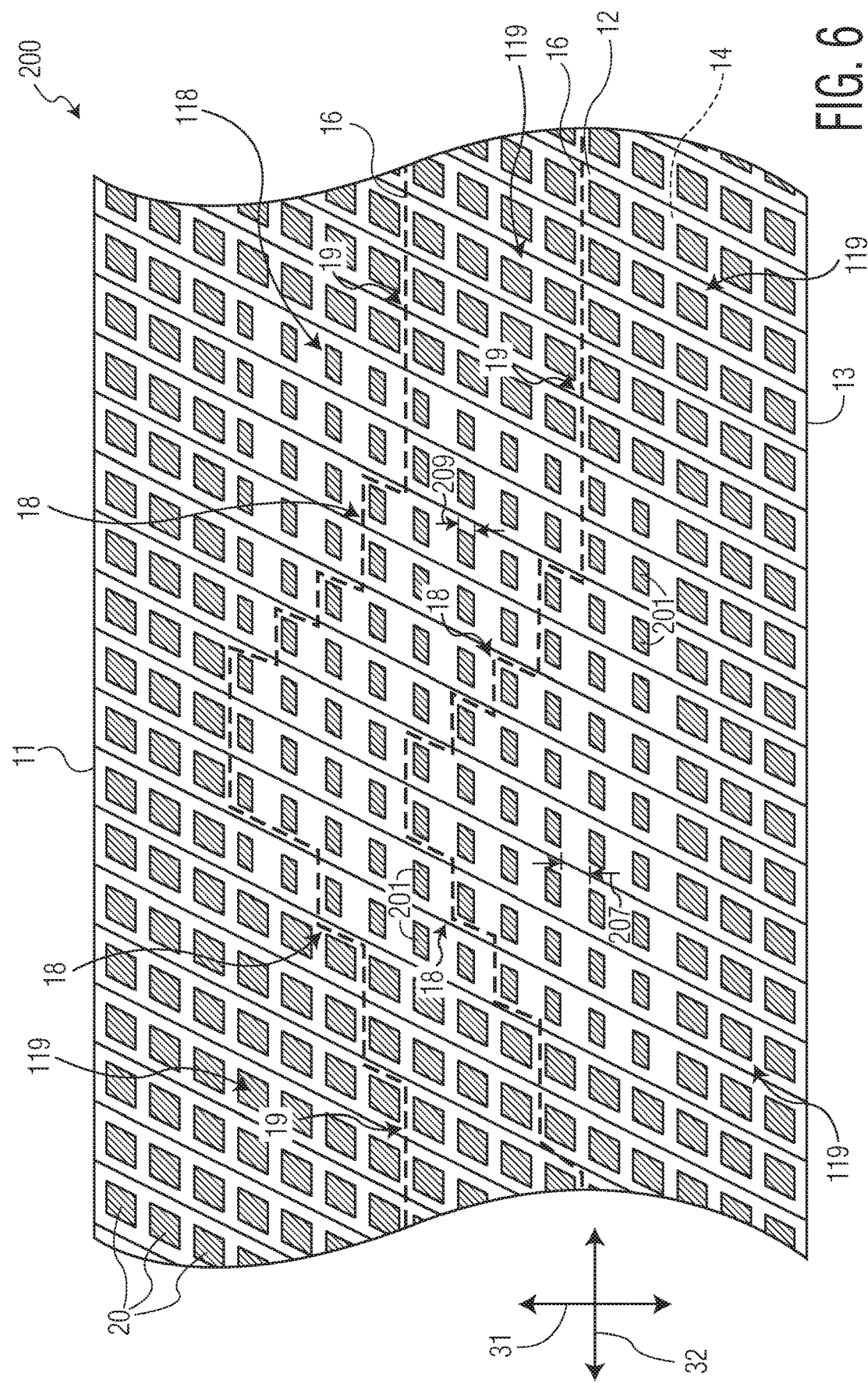
FIG. 6 is a plan view of another elasticated material according to aspects of the present disclosure.

As one example, FIG. 6 depicts exemplary elasticated material 200 comprising elastomeric strands 16 having arcuate portions 18. Like the exemplary materials 10, 10', the elastomeric strands 16 of the material 200 include both arcuate portions 18 and straight portions 19. However, unlike the materials 10, 10', the arcuate portions 18 of the elastomeric strands 16 extend through non-entrapping region 118. The bonds within the non-entrapping region 118 are labeled as bonds 201, and the bonds 201 have a different size than the bonds 20 which are disposed in the entrapping regions 119. More specifically, as shown in FIG. 6, the longitudinal height 209 of the bonds 201 may be less than the longitudinal height of the bonds 20 (e.g. height 44 as shown in FIG. 3A). As can be seen, this creates a larger longitudinal spacing between longitudinally adjacent bonds of the bonds 201, noted by longitudinal spacing 207, than the longitudinal spacing 25 of longitudinally adjacent bonds of the bonds 20 (as shown in FIG. 3A). Accordingly, in such embodiments as those similar to elasticated material 200, the longitudinal spacing 207 may be greater than an un-tensioned diameter of the elastomeric strands 16. In this manner, the non-entrapping region 118 comprising the bonds 201 may not allow for entrapment of the elastomeric strands 16 along their arcuate portions 18.

The non-entrapping regions 118 may be defined as the regions of the material 200 containing the bonds 201 which differ in size than the bonds 20, and where the differing size of the bonds 201 results in a longitudinal spacing 207 between longitudinally adjacent bonds 201 such that the bonds 201 do not allow for entrapment of the strands 16. Conversely, the entrapping regions 119 may be defined as the regions of the material 200 where the bonds 20 comprise a longitudinal spacing 25 between longitudinally adjacent bonds 20 which allows for entrapment of the strands 16.

The smaller dimension bonds 201 of the material 200 may help to prevent breakage of the elastomeric strands 16 during manufacture. For example, the effect of the smaller bond dimensions of the bonds 201 results in a relatively smaller average bonded area within the non-entrapping regions 118 of the material 200 through which the strands 16 may extend in a generally arcuate manner. This is in contrast to the relatively larger average bonded area of the regions of the materials 10, 10' through which the strands 16 extend in a generally straight manner. In some embodiments, the average bonded area of the material 200 in the entrapping regions 119 may be between about 5% to about 40%, or between about 5% and about 20%, or between about 10% and about 20%. The average bonded area of the material 200 in the non-entrapping regions may be between about 1% to about 10%. The smaller average bonded area of the non-entrapping regions 118 results in a lower chance that the strands 16 and the raised protrusions of the bonding element 54 which form the bonds 201 will align during the formation of the bonds 201. Accordingly, there is less chance that the process of bonding the layers 12 and 14 together will result in breakage of the strands 16.

Another way to define the materials of the present disclosure is by lateral regions. For example, the material 200 of FIG. 6 may be divided by longitudinal lines into separate lateral regions, such as lateral regions 128 and 129. The lateral regions 129 may be entrapping regions where the elastomeric strands within the regions 129 are entrapped, while the lateral regions 128 may be non-entrapping regions where the elastomeric strands are not entrapped (or at least not entrapped along a majority of their length within the regions 128). In such embodiments, the average bonded area within each of the regions 128, 129 may be different as described above. Generally, the average bonded area within the non-entrapping regions 128 may be less than the average bonded area within the entrapping regions 129. The average bonded area in the entrapping regions 129 may be between about 5% to about 40%, or between about 5% and about 20%, or between about 10% and about 20%. The average bonded area in the non-entrapping regions 128 may be between about 1% to about 10%.

Referring to material 200 of FIG. 6, although the one or more elastomeric strands 16 are not entrapped within the non-entrapping region 118 of the material 200, the bonds 201 maintain the generally arcuate or curved shape of the strands 16 within the non-entrapping region 118. For example, the material 200 is formed with the strands 16 under tension. When the material 200 is allowed to relax, the strands 16 will retract and press against the bonds 201, thereby maintaining the desired generally arcuate or curved shape of the strands 16 and imparting the material 200 with the desired stretch properties.

Figure 7:
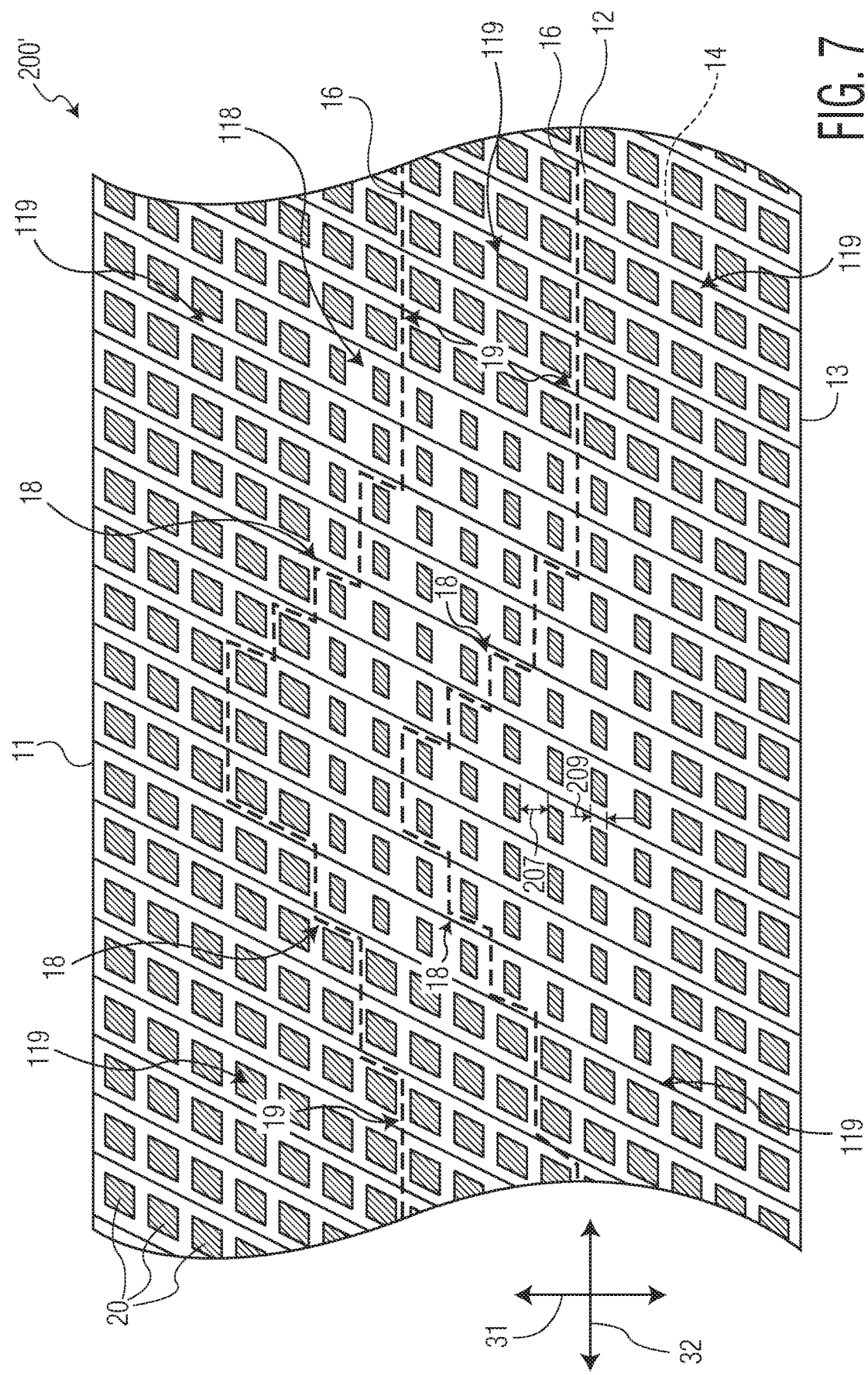
FIG. 7 is a plan view of another elasticated material according to aspects of the present disclosure.

The embodiment of material 200 in FIG. 6 shows the bonds 201 in the non-entrapping region 118 as generally aligning with laterally adjacent bonds 20 within the entrapping regions 119. For example, the top portions 34 of the bonds 201 and the bonds 20 generally align between laterally adjacent bonds of the bonds 201, 20. This is similar to the alignment of the bonds 20 in the described materials 10, 10'. However, the bonds 201, 20 do not need to align in this manner in all contemplated embodiments. For instance, FIG. 7 depicts another exemplary material, material 200', including one or more elastomeric strands 16 having a generally arcuate or curved shape. In the embodiment of FIG. 7, however, the bonds 201 in the non-entrapping regions 118 do not align with laterally adjacent bonds 20 in the entrapping regions 119 as in the materials 10, 10', and 200. As can be seen, the top portions 34 of the bonds 201, in the embodiment of material 200', do not align with the top portions 34 of laterally adjacent bonds 20. Instead, the bonds 201 are disposed such they are generally centered in the longitudinal direction 31 between top portions 34 and bottom portions 36 of laterally adjacent bonds 20.

Still further embodiments are contemplated by the present disclosure where one or more elastomeric strands extend through a non-entrapping region of an elasticated material in a generally arcuate or curved shape without being entrapped between bonds within the non-entrapping region. For example, instead of the bonds within a non-entrapping region having different dimensions than bonds outside of the non-entrapping region, additional elastomeric materials of the present disclosure are contemplated where the spacing between bonds within the non-entrapping region are different than the spacing between bonds outside of the non-entrapping region.

Figure 8:
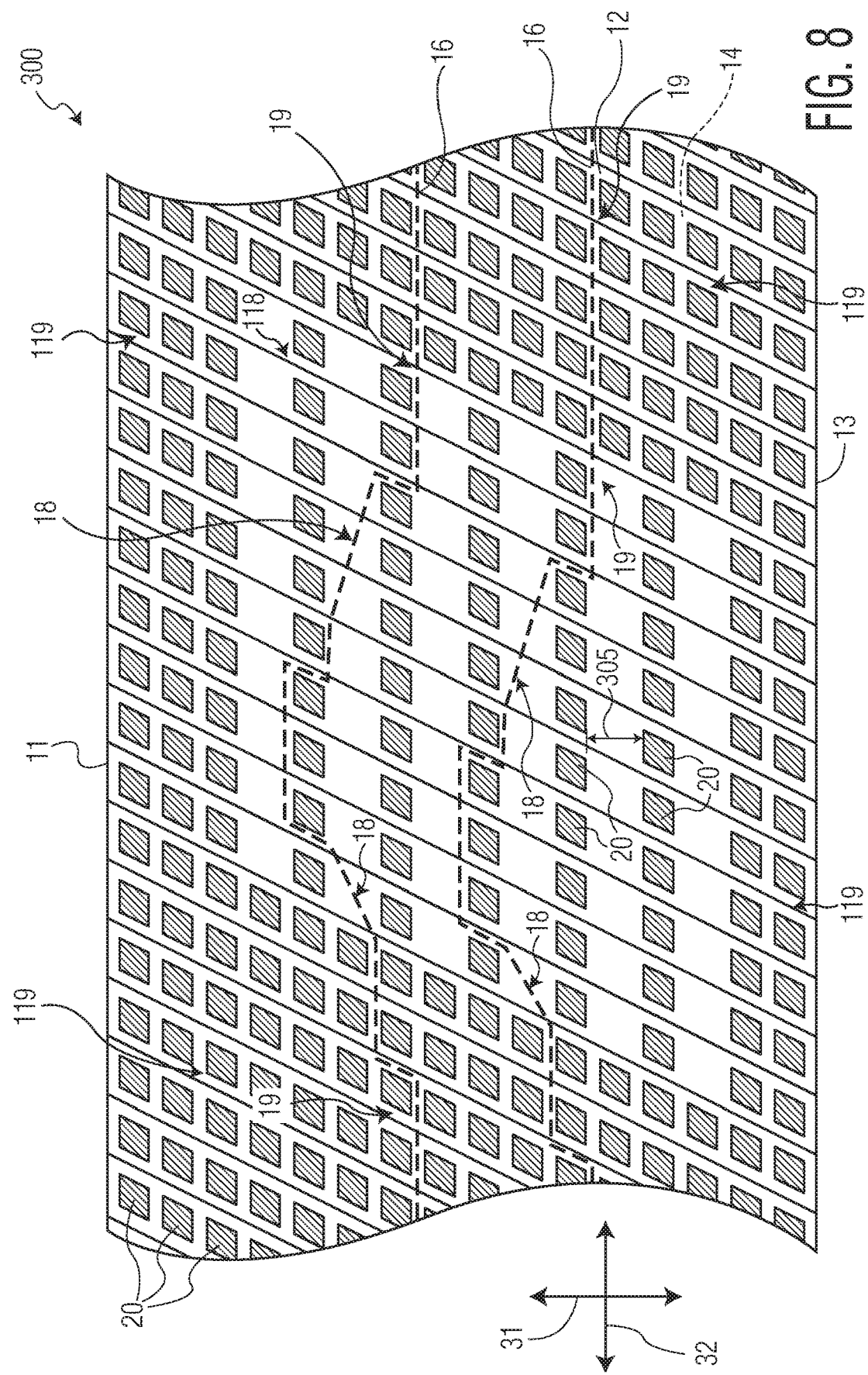
FIG. 8 is a plan view of another elasticated material according to aspects of the present disclosure.
Figure 9:
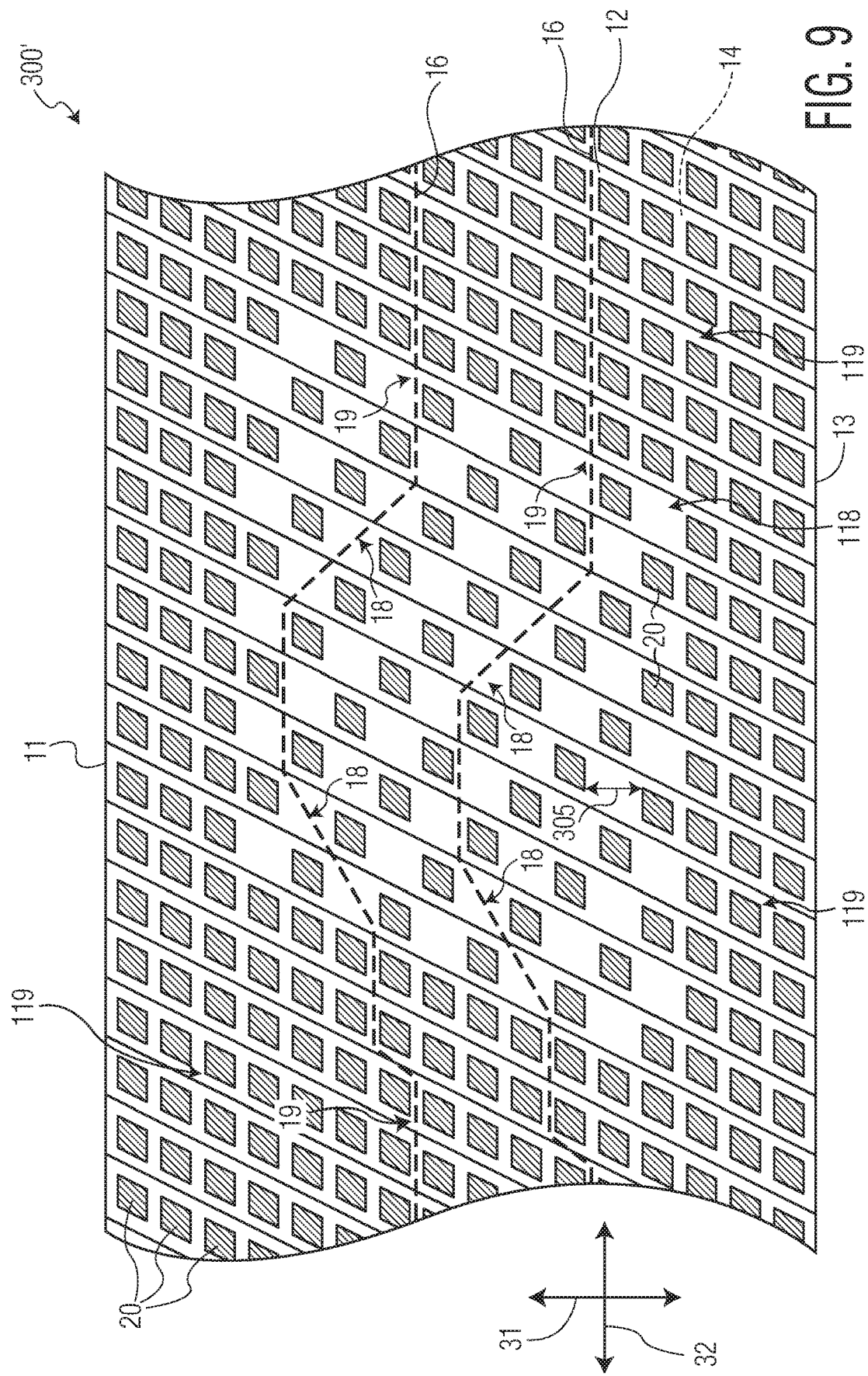
FIG. 9 is a plan view of another elasticated material according to aspects of the present disclosure.

FIGS. 8 and 9 depict additional exemplary materials 300, 300', respectively, according to aspects of the present disclosure. The exemplary materials 300, 300' depict embodiments of elasticated materials wherein the bonds within the non-entrapping regions 118 have a different spacing than bonds outside of the non-entrapping regions 118, for example within entrapping regions 119. For example, in the embodiment of FIG. 8, the bonds 20 within the non-entrapping region 118 and outside of the non-entrapping region 118 have generally the same size and shape, however the bonds 20 within the non-entrapping region 118 have a longitudinal spacing 305 between longitudinally adjacent bonds 20 that is greater than the longitudinal spacing 25 between bonds 20 outside of the non-entrapping region 118. Generally, the longitudinal spacing 305 is greater than the un-tensioned diameter of the elastomeric strands 16 so as to not allow entrapment of the strands 16 within the non-entrapping region 118. In the embodiment of FIG. 8, the non-entrapping region 118 is formed by removing every other longitudinally adjacent bond 20 to form the increased longitudinal bond spacing 305. Again, in such embodiments, the average bonded area within the non-entrapping region 118 is generally less than the average bonded area of the regions of the materials 10, 10' through which the strands 16 extend in a generally arcuate manner. The increased longitudinal spacing 305 may help to reduce the number of breakages of the elastomeric strands 16 during formation of the material 300 with respect to the formation of the materials 10 or 10'.

However, other embodiments may accomplish having a reduced average bonded area within non-entrapping regions while maintaining a similar bond size between bonds within non-entrapping regions and bonds outside of non-entrapping regions. For example, FIG. 9 depicts exemplary material 300' which includes non-entrapping region 118 comprising bonds 20 which are generally the same size as the bonds 20 outside of the non-entrapping region 118, for example the entrapping regions 119. In the embodiment of material 300', though, every other laterally adjacent bond of the bonds 20 within the non-entrapping region 118 is missing. Additionally, the first missing bond of the bonds 20 in each row alternates between longitudinally adjacent rows such that the longitudinal spacing between longitudinally adjacent bonds 20 within the non-entrapping region 118 is greater than the longitudinal spacing between longitudinally adjacent bonds 20 within the entrapping regions 119.

As in the material 300, the longitudinal spacing 305 between longitudinally adjacent bonds 20 within the non-entrapping region 118 in material 300' may be different than the longitudinal spacing 25 between the longitudinally adjacent bonds 20 in the entrapping regions 119. In general, the longitudinal spacing 305 is greater than the spacing 25, and more specifically greater than un-tensioned diameter of the elastomeric strands 16 so as to not allow entrapment of the strands 16 within the non-entrapping region 118. Like in the embodiment of FIG. 8, the elasticated material 300' in FIG. 9 also has a reduced average bond area within the non-entrapping region 118 than with respect to the average bonded area of the regions of the materials 10, 10' through which the strands 16 extend in a generally arcuate manner.

Figure 10:
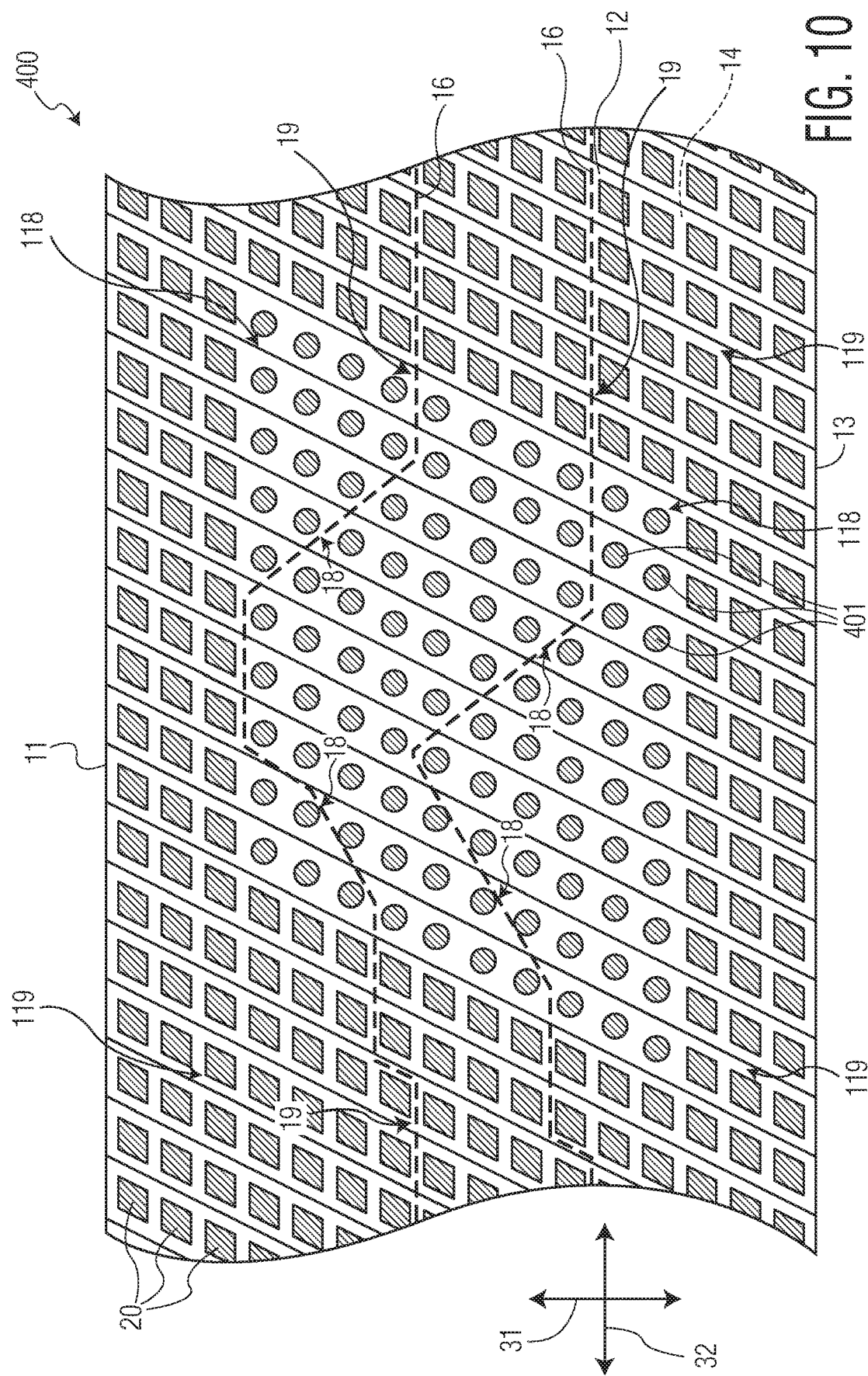
FIG. 10 is a plan view of another plan view of another elasticated material according to aspects of the present disclosure.
Figure 11:
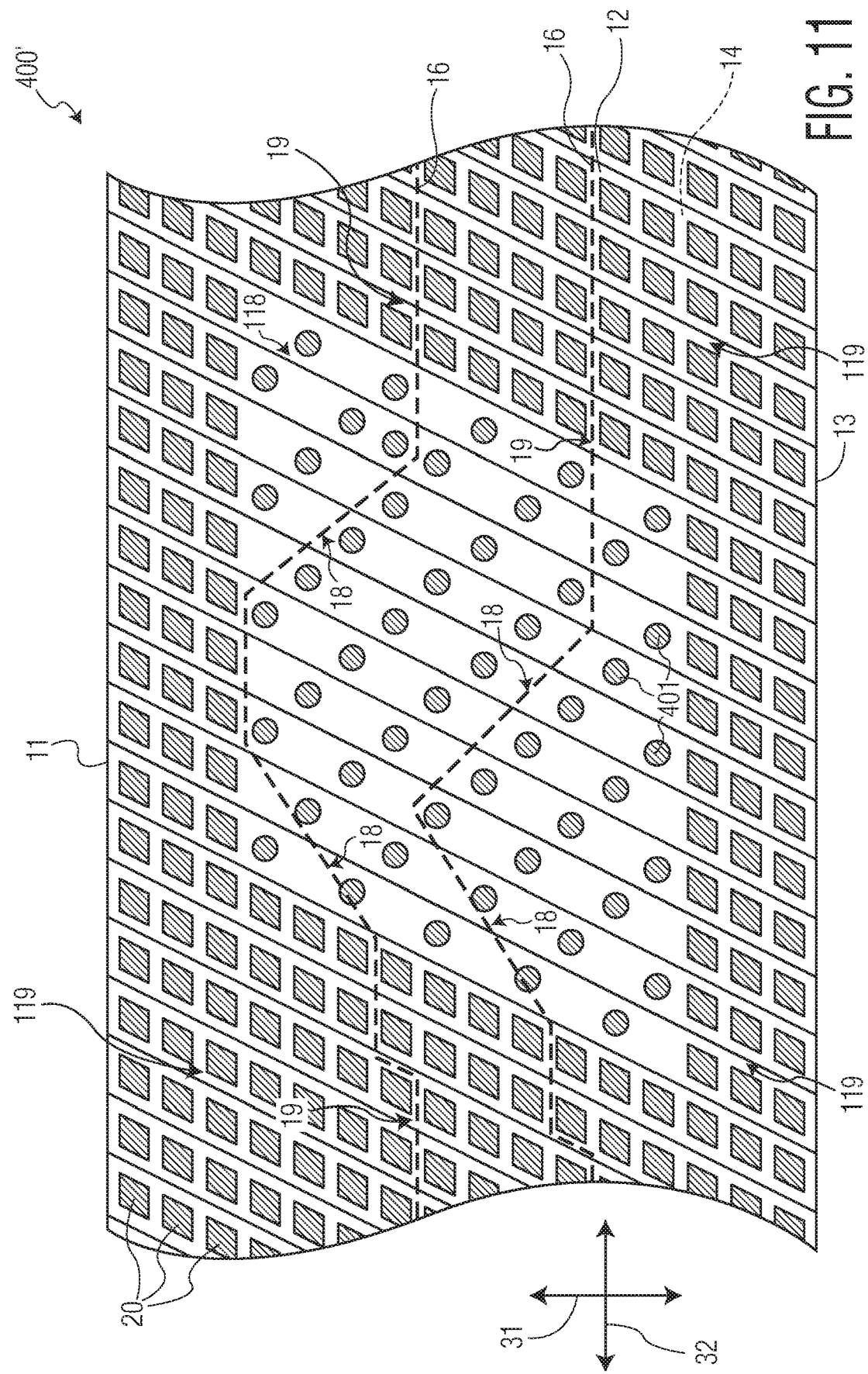
FIG. 11 is a plan view of another elasticated material according to aspects of the present disclosure.

Of course, in still further contemplated embodiments, the bonds within a non-entrapping region of an elasticated material may be both smaller in size than bonds outside of the non-entrapping region, as in the materials 200 and 200', and may also have relatively larger longitudinal spacing between longitudinally adjacent bonds within the non-entrapping region, as in the materials 300 and 300'. Additionally, it should be understood that the specific shape of the bonds within the non-entrapping regions and outside of the non-entrapping regions may differ as well. FIGS. 10 and 11 depict further exemplary elasticated materials 400 and 400', respectively, according to these aspects.

Elasticated material 400 of FIG. 10 is similar to elasticated material 200' in that the main difference between the bonds 401 within the non-entrapping region 118 and the bonds 20 outside of the non-entrapping region 118 is the bond size. However, in the embodiment of FIG. 10, the shape of the bonds 401 is also different than the shape of the bonds 20. Although the bonds 401 are shown as generally circular, the bonds 401 may be any suitable shape. Elasticated material 400' of FIG. 11 is similar to elasticated material 300' in that the longitudinal spacing of longitudinally adjacent bonds 401 within the non-entrapping region 118 is different than the longitudinal spacing of longitudinally adjacent bonds 20 outside of the non-entrapping region 118. The bonds 401 are also smaller than the bonds 20. Further, the shape of the bonds 401 in the embodiment of FIG. 11 within the non-entrapping region 118 is also different than the shape of the bonds 20 outside of the non-entrapping region 118. Although the bonds 401 are shown as generally circular, the bonds 401 may be any suitable shape.

Figure 12:
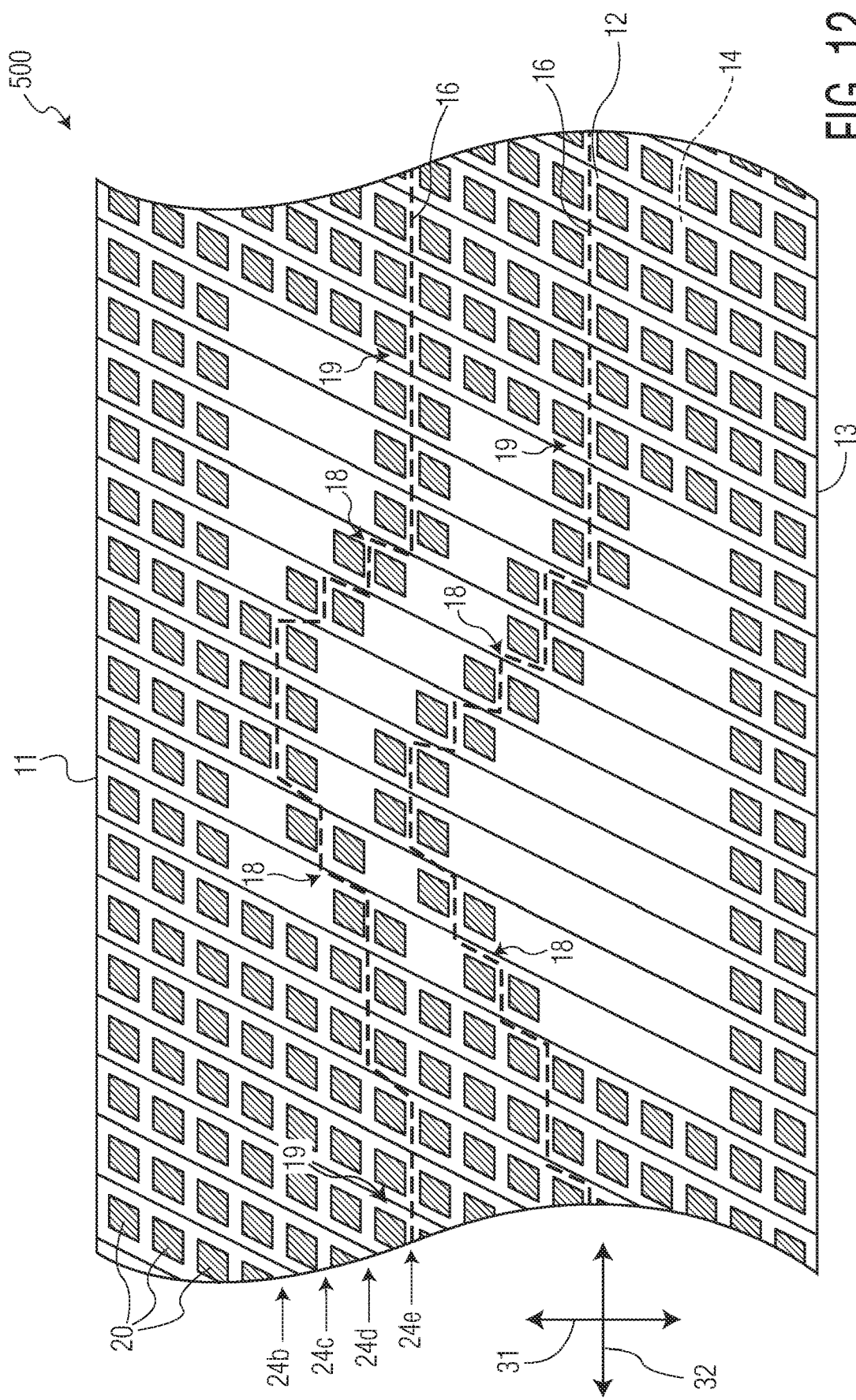
FIG. 12 is a plan view of another elasticated material according to aspects of the present disclosure.
Figure 13:
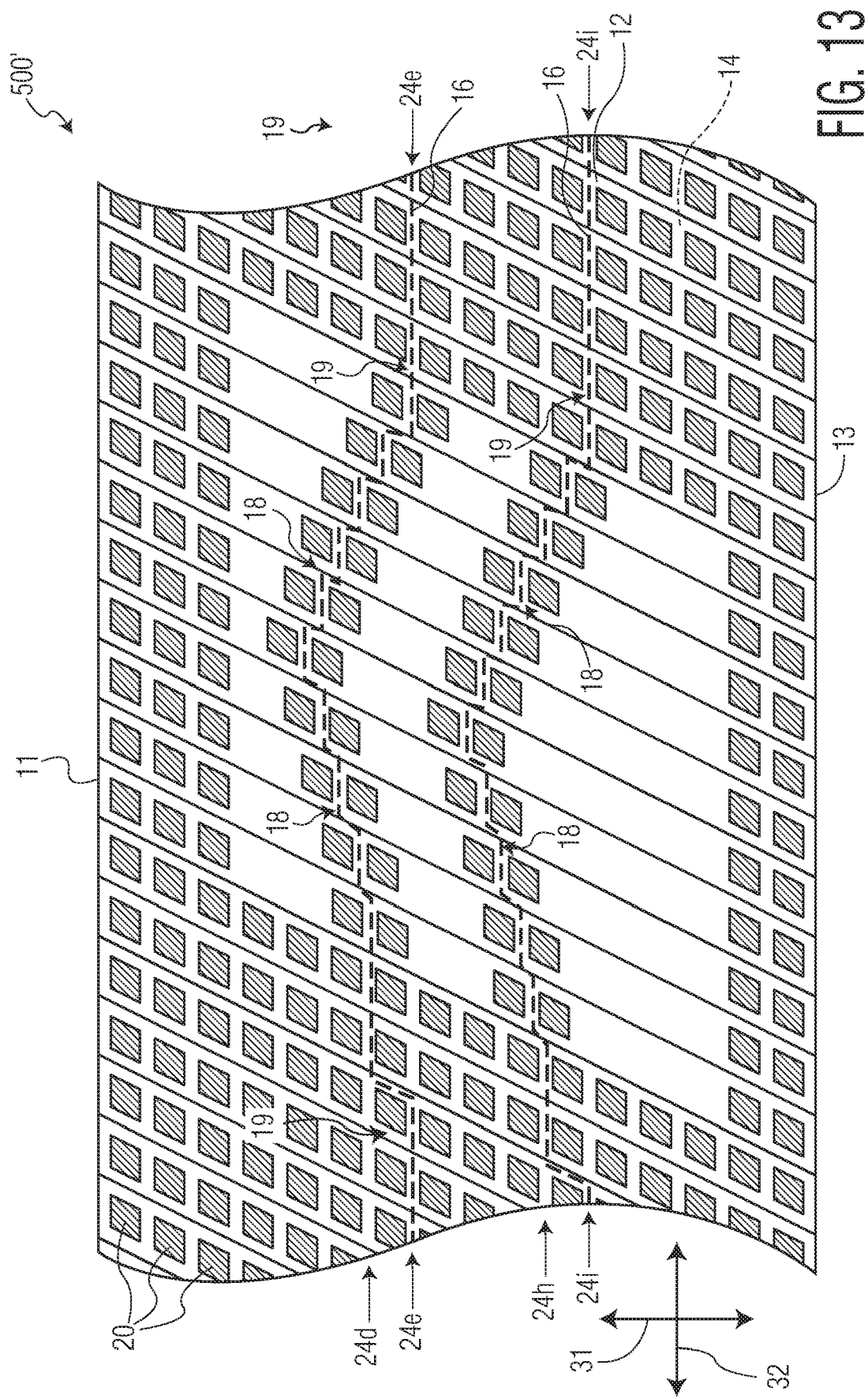
FIG. 13 is a plan view of another elasticated material according to aspects of the present disclosure.

FIGS. 12 and 13 depict further exemplary elasticated materials, materials 500, 500', according to aspects of the present disclosure. Such materials 500, 500' may be similar to materials 200 and 200', in that the elastomeric strands 16 may be entrapped along their arcuate portions 18. However, unlike the materials 200, 200', the material 500 may comprise only the bonds 20 which entrap the strands 16 along the arcuate portions 18 of the strands 16. For example, as can be seen in FIG. 12, the top strand 16 may extend through un-bonded channels 24e, 24d, 24c, and 24b, as in FIG. 1. However, in the embodiment of FIG. 12, the bonds 20 which form the portions of the unbonded channels 24e, 24d, 24c, and 24b through which the arcuate portions 18 of the strand 16 do not extend have been removed. In some embodiments, the bonds 20 which form the portions of the un-bonded channels which are longitudinally adjacent to the elastomeric strands 16 may be removed. For example, where the top elastomeric strand 16 in FIG. 12 extends through un-bonded channel 24c, the bonds which form (the longitudinally adjacent) un-bonded channels 24b and 24d have been removed. In this manner, the un-bonded channels 24b, 24d do not exist in the region of the material 500 longitudinally adjacent to the top elastomeric strand 16 where it extends through un-bonded channel 24c. In further embodiments, the bonds 20 forming the two-closest, longitudinally adjacent (e.g. two-above and two-below) un-bonded channels to the un-bonded channel through which an arcuate portion 18 of an elastomeric strand 16 extends may be removed. In further embodiments, the bonds 20 may be removed which form the closest three (3) to fifty (50) longitudinally adjacent un-bonded channels.

One advantage of such an embodiment is that the average bonded area of the material 500 in the region encompassing the arcuate portions 18 of the strand 16 is lower than the average bonded area of the material 500 outside of the region encompassing the arcuate portions 18 of the strand 16. In these embodiments, there may be less of a chance of one or more of the elastomeric strands 16 becoming broken or otherwise damaged during manufacture. For example, there may be less of a chance of one of the strands 16 aligning with a protrusion on the bonding element 54 if the strand 16 did not settle into a region between the protrusions of the bonding element 54 which form the bonds 20 which form the desired un-bonded channels through which the arcuate portions 18 of the strand 16 would extend.

In the embodiment of FIG. 13, the strands 16 of the elasticated material 500' are also entrapped along the arcuate portions 18. However, the elasticated material 500' comprises a differing bond pattern within the region of the material 500' encompassing the arcuate portions 18 of the strands 16. For example, instead of removing the bonds 20 which form portions of longitudinally adjacent un-bonded channels, the bonds 20 of the material 500' form a continuous, arcuate un-bonded channel through which the elastomeric strands 16 can extend. In the embodiment of FIG. 13, the top strand 16 can be seen extending through un-bonded channel 24e and then through un-bonded channel 24d. Laterally adjacent bonds 20 within the region of material 500' encompassing the arcuate portions 18 of the strand 16 are shown having a slight longitudinal offset such that the un-bonded channel 24d forms an arcuate path through which the strand 16 extends. Similarly, the bottom strand 16 in FIG. 13 is depicted extending through un-bonded channel 24i and also through un-bonded channel 24h, which forms an arcuate path through which the bottom strand 16 extends.

Laterally adjacent bonds 20 which form the arcuate un-bonded channels may have longitudinal offsets of anywhere between about 5% to about 100%, or between about 5% and about 75%, or between about 5% and about 50%. These lateral offset numbers represent a range of distances which laterally adjacent bonds 20 may be offset in the longitudinal direction 31. That is, instead of laterally adjacent bonds 20 fully overlapping each other in the lateral direction 32, a bond 20 may be may be shifted longitudinally up or down with respect to a laterally adjacent bond 20 by the described percentages, wherein the described percentages represent a percentage of a height dimension of the bonds 20 (e.g. such as height 44 or 209).

Due to the differing bond pattern in the region of the material 500' encompassing the arcuate portions 18 of the strand 16, the average bond area within this region may be lower than in regions of the material 500' which do not encompass the arcuate portions 18 of the strand 16. Accordingly, similar to elasticated material 500, there may be less of a chance of one or more of the elastomeric strands 16 becoming broken or otherwise damaged during manufacture, for example if one or more of the strands 16 did not align with the regions between the protrusions on one of the bonding elements while the one or more stands are oscillating.

Of course, although the un-bonded channels through which the arcuate portions 18 of the elastomeric strands 16 extend were shown and described in FIGS. 12 and 13 as entrapping the strands 16, this may not be the case in all embodiments. In some embodiments of the materials 500 and 500', the bonds 20 may be disposed on opposite sides of the strands 16 along the arcuate portions 18 and spaced a distance greater than the un-tensioned diameter of the elastomeric strands 16. Such embodiments may be advantageous because the strands 16 may be less likely to be broken or otherwise damaged during manufacture. For example, it may be easier for the arcuate portions 18 of the strands 16 to settle between the relatively larger spaces located in-between the protrusions of the bonding element 54 prior to the protrusions forming the bonds 20.

Figure 14:
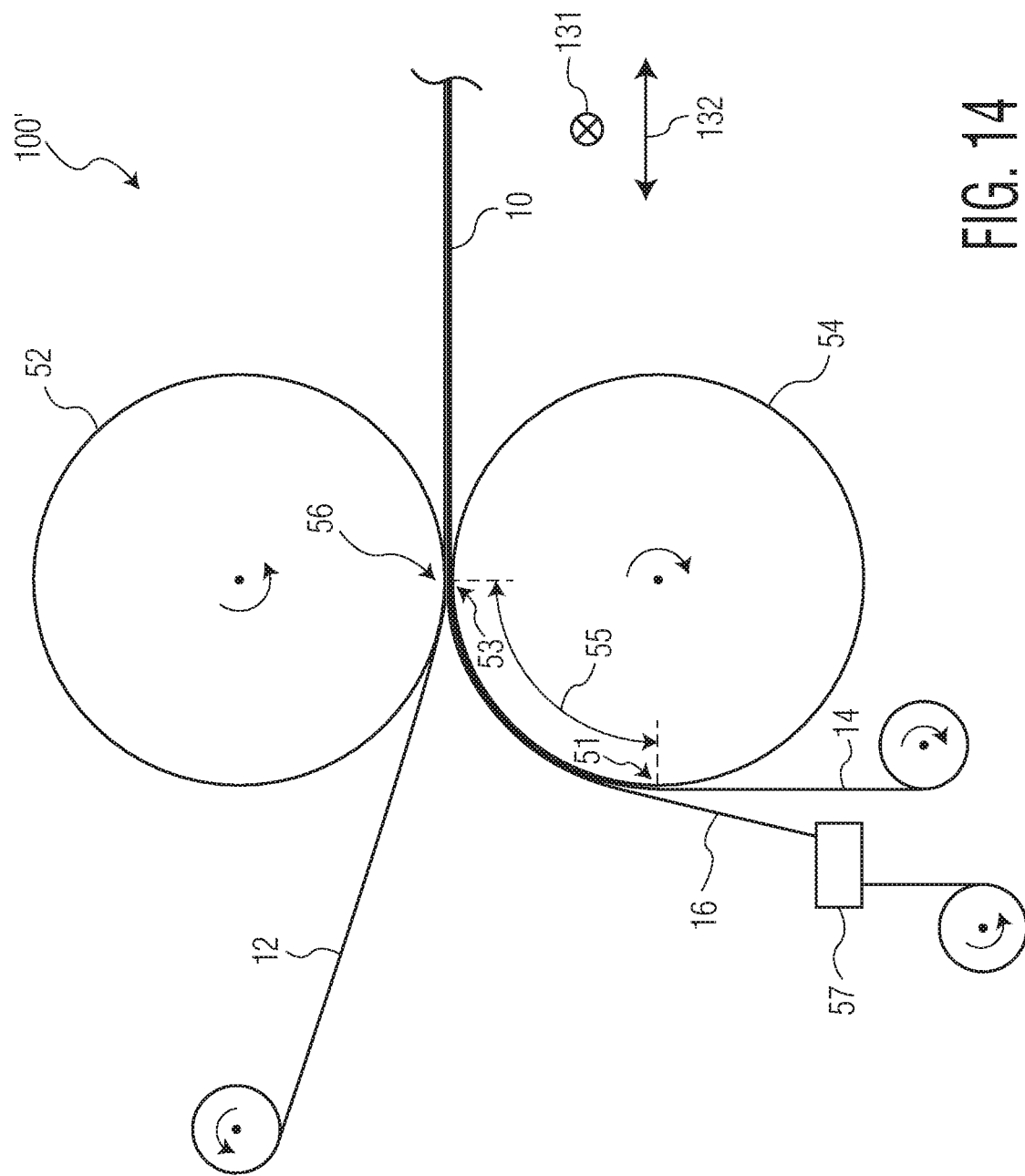
FIG. 14 is a schematic view of a process for forming elasticated materials of the present disclosure.
Figure 15:
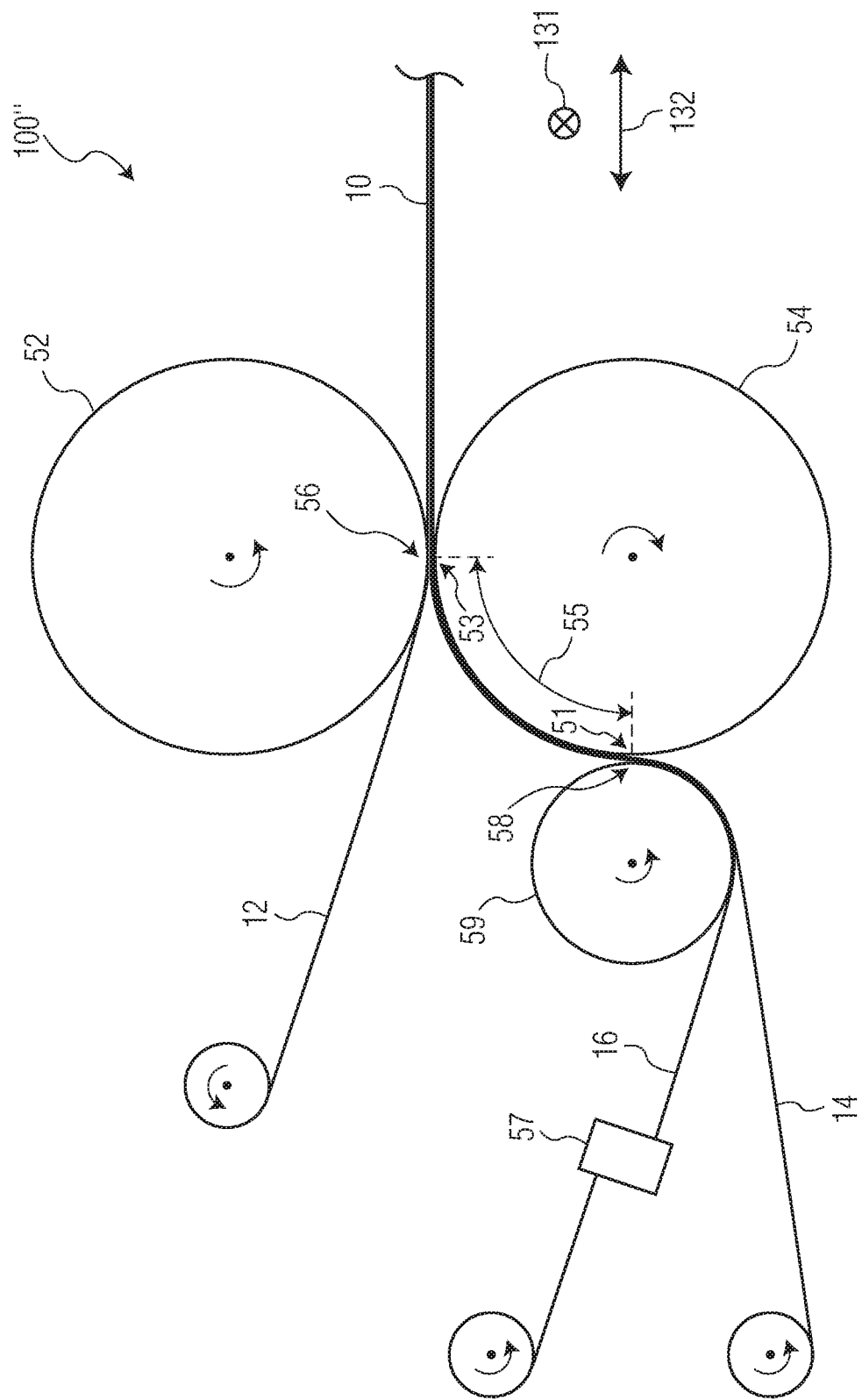
FIG. 15 is another schematic view of a process for forming elasticated materials of the present disclosure.

Instead of adjusting the bond pattern to form elasticated materials with entrapping regions 119 and non-entrapping regions 118, adjustments to the process 100 may be made which will also help to minimize breakage of the strands 16 during manufacture. For example, FIGS. 14 and 15 depict alternative exemplary apparatuses for performing processes 100' and 100" for forming elasticated materials according to the present disclosure.

The process 100' is similar to the process 100 described with respect to FIG. 5. However, the process 100' further comprises a step of contacting the bonding element 54 with the one or more elastomeric strands 16 prior to the bonding nip 56. As can be seen in FIG. 14, the one or more elastomeric strands 16 contact the bonding element 54 at contact point 51 disposed on the circumference of the bonding element 54. As used herein, the term "contact" is not limited to only physical contact. Instead, the term "contact" includes states where a first component is pressed against a second component with one or more intervening layers preventing direct contact between the first and second components. For instance, in the above example, the one or more elastomeric strands 16 do not directly contact the bonding element 54 because the second layer of material is disposed between the one or more elastomeric strands 16 and the bonding element 54. However, as used herein, the one or more elastomeric strands 16 are still considered to be in contact with the bonding element 54.

The one or more elastomeric strands 16 then wrap around the bonding element 54 for a distance 55 extending between contact point 51 and contact point 53 on the circumference of the bonding element 54, which coincides with the bonding nip 56. Accordingly, distance 55 may represent a circumferential distance. In order to have a low-occurrence of breakage of the one or more elastomeric strands 16 at the bonding nip 56, the distance 55 should be between about 5% and about 75% of the overall circumference of the bonding element 54. In other embodiments, the distance 55 should be between about 5% and about 50%, or between about 5% and about 45%, or between about 10% and about 40%, or between about 15% and about 35%, or between about 20% and about 30%, of the overall circumference of the bonding element 54.

By contacting the bonding element 54 along its circumference for the distance 55 prior to the bonding nip 56, the one or more elastomeric strands 16 are able to settle into regions between the raised protrusions of the bonding element 54 prior to reaching the bonding nip 56. Accordingly, because the one or more elastomeric strands 16 are disposed between the raised protrusions once they reach the bonding nip 56, the one or more elastomeric strands 16 are not in danger of being broken by the protrusions of the bonding element 54 during the bonding of the first layer 12 to the second layer 14.

FIG. 15 is an alternative apparatus for practicing the process 100". The apparatus depicted in FIG. 15 is similar to the apparatus depicted in FIG. 12, including bonding elements 52 and 54. However, the apparatus shown in FIG. 13 further includes guide element 59. Guide element 59 is disposed adjacent bonding element 54, forming guide nip 58. In the specific embodiment of FIG. 13, the guide element 59 is a guide roll. Guide element 59 helps to ensure contact between the second layer 14 and the one or more elastomeric strands 16 and the bonding element 54 prior to the bonding nip 56. The guide element 59 may be positioned with respect to the bonding element 54 such that the guide nip 58 is disposed the circumferential distance 55 away from the bonding nip 56. In alternative embodiments to that shown in FIG. 15, the first layer of material 12 may also be positioned to also extend through the guide nip 56 as does the second layer of material 14 and the one or more elastomeric strands 16.

It should be understood that any of the above embodiments may be combined with any of the other described embodiments in any combinations. For example, FIG. 11 depicted an exemplary elasticated material 400' which combined the features of materials 200' and 300' where the bonds 401 within non-entrapping region 118 have both a different (greater) longitudinal spacing between longitudinally adjacent bonds 401 than the longitudinal spacing between longitudinally adjacent bonds 20 within entrapping regions 119, along with the bonds 401 having a smaller size than the bonds 20. The elasticated material 400' could be made according to any of the described processes 100, 100', or 100". In some embodiments of the present disclosure, contemplated elasticated materials may have any bond pattern described herein, or any other suitable bond pattern, and be made according to any one of the processes 100, 100', or 100". Although the bond patterns comprising non-entrapping regions 118 were described as useful for making elasticated materials having elastomeric strands with arcuate portions easier to manufacture, nothing in this disclosure should be construed as preventing such bond patterns being formed according to the process 100' or 100", both of which are also described as helping to make the manufacture elasticated materials having elastomeric strands with arcuate portions easier.

Of course, any of the above described elasticated materials may be used within various different clothing garments and absorbent articles. For instance, the disclosed elasticated materials may form at least a portion of a waistband or waist panel of a clothing garment or absorbent article, or at least a portion of elastomeric leg cuffs of a clothing garment or absorbent article. The disclosed materials may be used within other portions of absorbent articles such as within an absorbent core of an absorbent article, as part of a containment flap of an absorbent article, or as part of a surge and/or distribution layer of an absorbent article.

Figure 16:
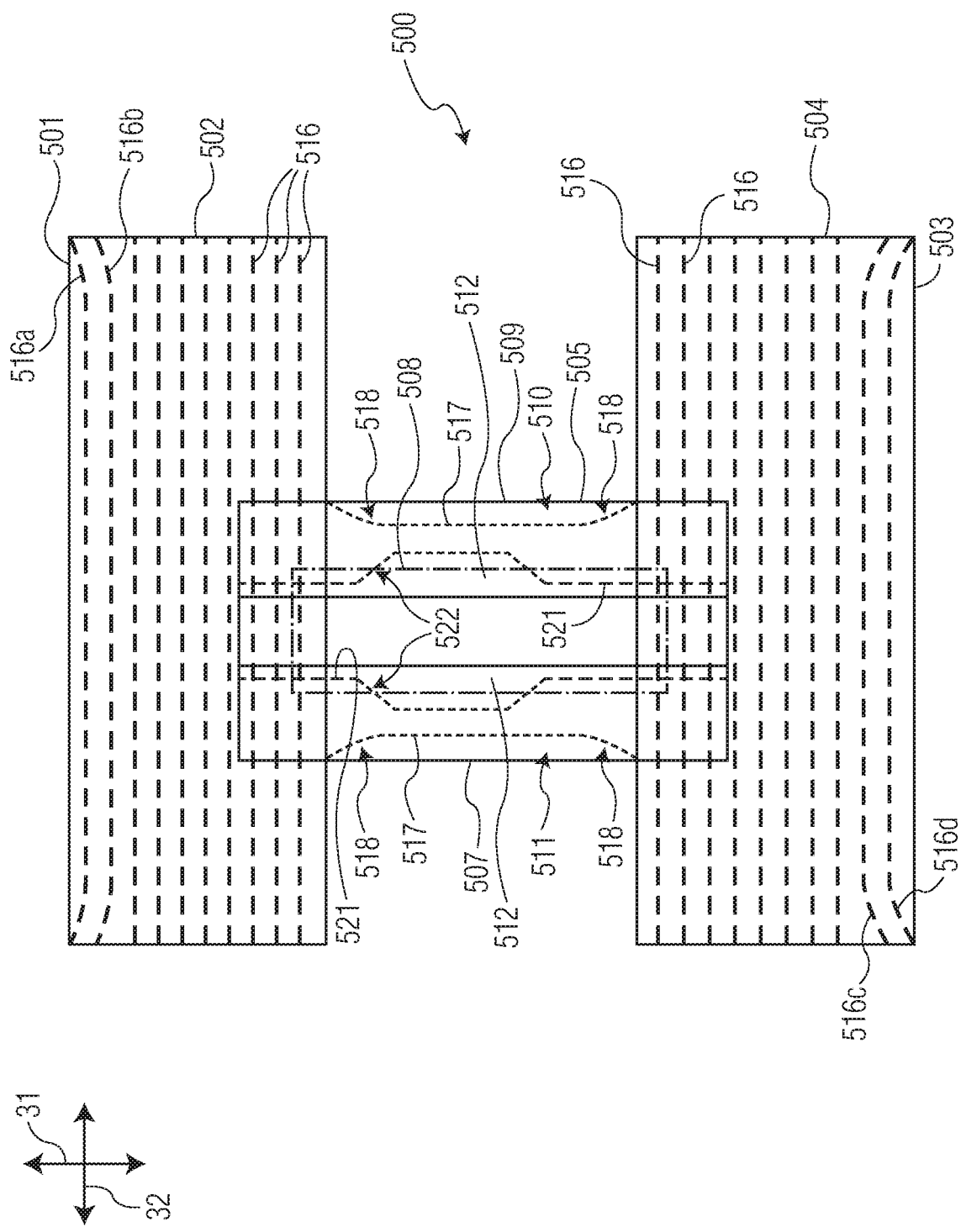
FIG. 16 is an exemplary absorbent article including elasticated materials according to aspects of the present disclosure.

FIG. 16 depicts exemplary absorbent article 500 which includes elasticated materials as part of its waistbands, leg cuffs, and containment flaps. The embodiment of FIG. 16 illustrates absorbent article 500 which comprises an absorbent article manufactured in what is commonly termed a cross-machine direction (CD) process. However, it should be understood that other absorbent articles which are manufactured in machine-direction (MD) processes may contain elasticated materials according to the present disclosure without departing from the spirit and scope of the disclosure.

The absorbent article 500 can comprise a three-piece construction where the absorbent article 500 has a chassis 506 including a front waist panel 502 having a front waist edge 501, a rear waist panel 504 having a rear waist edge 503, and an absorbent panel 509 extending between the front waist panel 502 and the rear waist panel 504. The absorbent panel 509 may generally include absorbent body 508.

In some embodiments, the absorbent panel 509 can have a first lateral side edge 505 and a second lateral side edge 507 and can overlap the front waist panel 502 and the rear waist panel 504. The absorbent panel 509 can be bonded to the front waist panel 502 and the rear waist panel 504 to define a three-piece construction. However, it is contemplated that an absorbent article can be manufactured in a CD process without being a three-piece construction garment, which is also sometimes referred to as a one-piece construction (not shown), as the front waist panel 502 and the rear waist panel 504 are integral with one another by way of commonly connected components forming the waist panel such as a bodyside liner and/or an outer cover which can envelope the absorbent panel 509 or simply cover the garment side of the absorbent panel 509.

The front waist panel 502 and the rear waist panel 504 may generally comprise elastomeric strands 516 disposed between at least two layers of material. For instance, the front waist panel 502 and the rear waist panel 504 may comprise an elasticated material such as those as described herein. These different embodiments may impart different beneficial fit properties to the absorbent article 500. For example, one or more of the strands 516 may extend throughout at least a portion of the front and/or rear waist panels 502, 504 in an arcuate manner, such as strands 516a-d. These arcuate strands 516, or portions of the strands 516, may allow for a closer and/or more comfortable fit of the article 500 when worn, such as by providing better contouring of the article 500 on a body.

Similarly, leg cuffs 510, 511 may be formed with one or more elastomeric strands 517. In some embodiments, portions 518 of one or more of the strands 517 may extend in an arcuate manner, according to any of the embodiments described herein. This may allow for a better fit of the article 500 where the leg cuffs 510, 511 are better able to conform to a wearers body, such as around the legs. In some additional or alternative embodiments, containment flaps 512 may also comprise one or more elastomeric strands 521. At least some portions, such as portions 522, of these elastomeric strands 521 may extend in an arcuate manner, according to any of the embodiments described herein, so as to better conform to a wearer's body to help preventing leaking.

Figure 17:
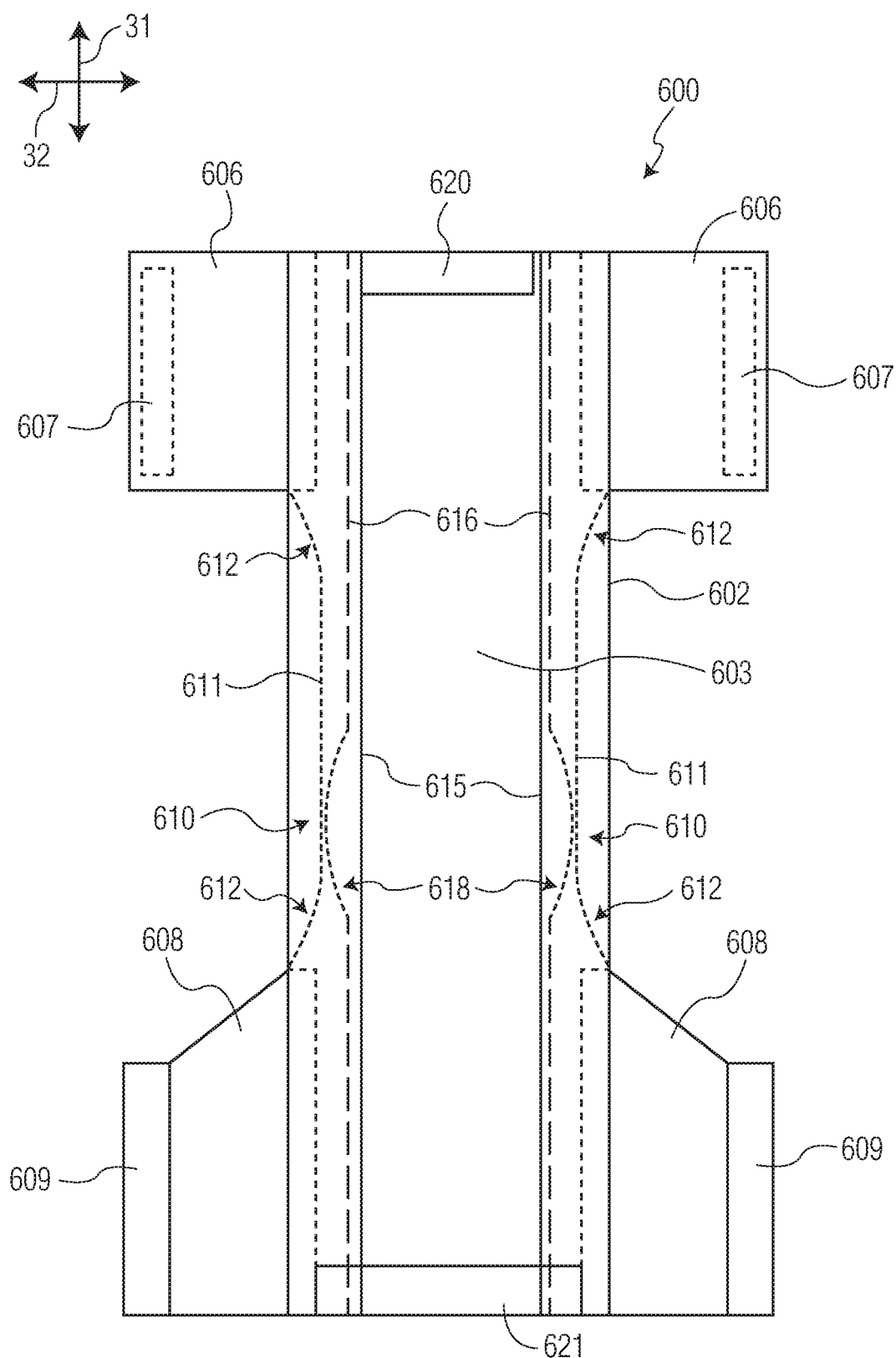
FIG. 17 is another exemplary absorbent article including elasticated materials according to aspects of the present disclosure.

FIG. 17 depicts another exemplary absorbent article 600 which may benefit from using one or more of the materials disclosed herein. The article 600 includes chassis 602 and body facing surface 603 and may further include front side panels 609 and rear side panels 608. The front side panels 609 may include attachment region 607, while the rear side panels 608 may include attachment region 609. The attachment regions 607, 609 may cooperate with one another to from a secure connection between the front side panels 609 and the rear side panels 609. In such a configuration, the article 600 may be considered to be in a wear configuration.

In some embodiments, it may be beneficial for at least one of the front side panels 609 and/or the rear side panels 608 to comprise one or more elastomeric strands that have one or more arcuate portions (not shown). Accordingly, front side panels 609 and/or the rear side panels 608 may comprise any of the materials described herein. The front side panels 609 and/or the rear side panels 608 may benefit from implementation of elastomeric strands having arcuate portions to in order to provide a better fit for article 600. Since the front side panels 609 and/or the rear side panels 608 sit extend around a portion of a waist and legs of a wearer, the arcuate portions of elastomeric strands of the front side panels 609 and/or the rear side panels 608 may provide for better contouring of the article 600 resulting in a better fit.

Article 600 may further comprise leg cuffs 610, which may be formed with one or more elastomeric strands 611. In some embodiments, portions of one or more of the strands 611 may extend in an arcuate manner, such as portions 612, according to any of the embodiments described herein. This may allow for a better fit of the article 600 where the leg cuffs 610 are better able to conform to a wearer's body, such as around the legs. In some additional or alternative embodiments, containment flaps 615 may also comprise one or more elastomeric strands 616. At least some portions of these elastomeric strands 616, such as portions 618, may extend in an arcuate manner according to any of the embodiments described herein. These arcuate portions 618 may allow the containment flaps 615 to better conform to a wearer's body to help preventing leaking. In still further additional or alternative embodiments, the article 600 may comprise a front waistband 620 and/or a rear waistband 621. In various embodiments, the front waistband 620 and/or a rear waistband 621 way comprise one or more elastomeric strands which extend in an arcuate manner, according to any of the materials disclosed herein. Such arcuate portions in the front waistband 620 and/or a rear waistband 621 may help provide the article 600 with a better fit characteristic.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

Those skilled in the art will recognize that the present disclosure may be manifested in a variety of forms other than the specific embodiments described and contemplated herein. Specifically, the various features described with respect to the various embodiments and figures should not be construed to be applicable to only those embodiments and/or figures. Rather, each described feature may be combined with any other feature in various contemplated embodiments, either with or without any of the other features described in conjunction with those features. Accordingly, departure in form and detail may be made without departing from the scope of the present disclosure as described in the appended claims.

Embodiments

In a first embodiment, a method for forming an elasticated material may comprise advancing a first continuous substrate material having an upper surface and a lower surface in a machine direction, advancing a second continuous substrate material having an upper surface and a lower surface in the machine direction, and advancing an elastomeric strand in a stretched state in the machine direction, wherein the elastomeric strand is positioned between the lower surface of the first continuous substrate material and the upper surface of the second continuous substrate material. The method may further comprise advancing the first continuous substrate material and the second continuous substrate material with the elastomeric strand positioned therebetween to a bonding apparatus. The bonding apparatus may comprise a first bonding element and a second bonding element disposed proximate the first bonding element and forming a bonding nip with the first bonding element. The method may also comprise oscillating the elastomeric strand in a cross-machine direction, advancing the first continuous substrate material, the second continuous substrate material, and the elastomeric strand through the bonding nip and bonding the first continuous substrate material to the second continuous substrate material with the elastomeric strand disposed therebetween with at least a first bond and a second bond. The first bond and the second bond may be disposed on opposite sides of the elastomeric strand and spaced apart a distance less than an un-tensioned diameter of the elastomeric strand and may be located along a portion of the elastomeric strand which extends in an arcuate manner.

In a second embodiment, the second bonding element of the first embodiment may have an outer edge comprising a circumference, and the second continuous substrate and the elastomeric strand may contact the second bonding element along the outer edge for a contact length that is between about 5% and about 75% of the circumference.

In a third embodiment, the second bonding element of any of the first and second embodiments may be a roll having an outer edge comprising a circumference, and the second continuous substrate and the elastomeric strand may contact the second bonding element along the outer edge for a contact length that is between about 15% and about 50% of the circumference.

In a fourth embodiment, the first continuous substrate material of the second embodiment may contact the second bonding element along the outer edge for a contact length that is between about 5% and about 75% of the circumference.

In a fifth embodiment, the step of bonding the first continuous substrate material to the second continuous substrate material with the elastomeric strand disposed therebetween of any of the first through fourth embodiments may further comprise forming a third bond and a fourth bond disposed on opposite sides of the elastomeric strand. The third bond and the fourth bond may be spaced apart a distance less than an un-tensioned diameter of the elastomeric strand and located along a portion of the elastomeric strand which extends in a straight manner.

In a sixth embodiment, the method of any of the first through fifth embodiments may not include a step of applying adhesive between the first continuous substrate material and the second continuous substrate material.

In a seventh embodiment, the first bond and the second bond of any of the first through sixth embodiments may be formed by pressure bonding.

In an eighth embodiment, the first bond and the second bond of any of the first through sixth embodiments may be formed by ultrasonic bonding.

In a ninth embodiment, a method for forming an elasticated material may comprise advancing a first continuous substrate material having an upper surface and a lower surface in a machine direction, advancing a second continuous substrate material having an upper surface and a lower surface in the machine direction, advancing an elastomeric strand in a stretched state in the machine direction, wherein the elastomeric strand is positioned between the lower surface of the first continuous substrate material and the upper surface of the second continuous substrate material, and advancing the first continuous substrate material and the second continuous substrate material with the elastomeric strand positioned therebetween to a bonding apparatus. The bonding apparatus may comprise a first bonding element, a second bonding element disposed proximate the first bonding element and forming a bonding nip with the first bonding element, and a guide element disposed proximate the second bonding element and forming a guide nip with the second bonding element. The method may further comprise oscillating the elastomeric strand in a cross-machine direction, advancing the second continuous substrate and the elastomeric strand through the guide nip so that the second continuous substrate and the elastomeric contact the second bonding element prior to the bonding nip, and advancing the first continuous substrate material, the second continuous substrate material, and the elastomeric strand through the bonding nip and bonding the first continuous substrate material to the second continuous substrate material with the elastomeric strand disposed therebetween with at least a first bond and a second bond. The first bond and the second bond may be disposed on opposite sides of the elastomeric strand and spaced apart a distance less than an un-tensioned diameter of the elastomeric strand and located along a portion of the elastomeric strand which extends in an arcuate manner.

In a tenth embodiment, the second bonding element of the ninth embodiment may be a roll having an outer edge comprising a circumference, and the guide nip may be disposed such that a distance between the bonding nip and the guide nip, along the outer edge of the second bonding element, is between about 5% and about 75% of the circumference.

In an eleventh embodiment, the second bonding element of any of the ninth and tenth embodiments may be a roll having an outer edge comprising a circumference, and the guide nip may be disposed such that a distance between the bonding nip and the guide nip, along the outer edge of the second bonding element, is between about 15% and about 50% of the circumference.

In a twelfth embodiment, the method of any of the ninth through eleventh embodiments may further comprise advancing the first continuous substrate material through the guide nip along with the second continuous substrate material and the first continuous substrate material.

In a thirteenth embodiment, the step of bonding the first continuous substrate material to the second continuous substrate material with the elastomeric strand disposed therebetween of any of the ninth through twelfth embodiments may further comprise forming a third bond and a fourth bond disposed on opposite sides of the elastomeric strand. The third bond and the fourth bond may be spaced apart a distance less than an un-tensioned diameter of the elastomeric strand and located along a portion of the elastomeric strand which extends in a straight manner.

In a fourteenth embodiment, the method of any of the ninth through thirteenth embodiments may not include a step of applying adhesive between the first continuous substrate material and the second continuous substrate material.

In a fifteenth embodiment, the first bonding element and the second bonding element of any of the ninth through fourteenth embodiments may comprise rolls.

In a sixteenth embodiment, an elasticated material may comprise a first substrate layer, a second substrate layer, an elastomeric strand disposed between the first substrate layer and the second substrate layer, and a plurality of bonds bonding the first substrate layer to the second substrate layer.

The elastomeric strand may comprise at least one straight portion and at least one arcuate portion. The plurality of bonds may comprise a first bond and a second bond, and the first bond and the second bond may be disposed on opposite sides of the elastomeric strand and spaced apart a distance less than an un-tensioned diameter of the elastomeric strand and located along an arcuate portion of the elastomeric strand.

In a seventeenth embodiment, the plurality of bonds further of the sixteenth embodiment may further comprise a third bond and a fourth bond, and the third bond and the second bond may be disposed on opposite sides of the elastomeric strand. The third bond and the fourth bond may be spaced apart a distance less than an un-tensioned diameter of the elastomeric strand located along the at least one straight portion of the elastomeric strand.

In an eighteenth embodiment, the material of any of the sixteenth and seventeenth embodiments may not include adhesive.

In a nineteenth embodiment, the plurality of bonds of any of the sixteenth through eighteenth embodiments may be disposed in bond rows forming a plurality of un-bonded channels extending between longitudinally adjacent bond rows, and the arcuate portion of the elastomeric strand may extend between multiple of the plurality of un-bonded channels.

In a twentieth embodiment, the plurality of bonds of any of the sixteenth through nineteenth embodiments may be disposed in bond rows forming a plurality of un-bonded channels extending between longitudinally adjacent bond rows and a portion of the plurality of bonds form may an un-bonded channel having an arcuate shape. Additionally, the arcuate portion of the elastomeric strand may extend through the arcuate un-bonded channel.

In a twenty-first embodiment, an elasticated material may extend in a lateral direction and a longitudinal direction and may comprise a first web of material and a second web of material bonded to the first web of material by a plurality of bonds. The plurality of bonds may comprise a first series of opposing bond pairs extending in the lateral direction, the first series of opposing bond pairs defining a first un-bonded channel extending between the first series of opposing bond pairs, and a second series of opposing bond pairs extending in the lateral direction and spaced longitudinally from the first series of opposing bond pairs, the second series of opposing bond pairs defining a second un-bonded channel extending between the second series of opposing bond pairs. The material may further comprise an elastomeric strand extending in the lateral direction and disposed between the first web of material and the second web of material. A first portion of the elastomeric strand may be disposed within the first un-bonded channel, and a second portion of the elastomeric strand may be disposed within the second un-bonded channel.

In a twenty-second embodiment, the bonds of at least one bond pair of the first series of opposing bond pairs, of the material of the twenty-first embodiment, which define a portion of the first un-bonded channel in which the elastomeric strand is situated may be spaced apart in the longitudinal direction a distance less than an un-tensioned diameter of the elastomeric strand.

In a twenty-third embodiment, the bonds of at least one bond pair of the first series of opposing bond pairs, of the material of the twenty-second embodiment, may be spaced apart in the longitudinal direction a distance greater than the un-tensioned diameter of the elastomeric strand.

In a twenty-fourth embodiment, the bonds which are spaced apart in the longitudinal direction a distance less than the un-tensioned diameter of the elastomeric strand, of the material of the twenty-third embodiment, may have first bond areas, the bonds which are spaced apart in the longitudinal direction a distance greater than the un-tensioned diameter of the elastomeric strand, of the material of the twenty-third embodiment, may have second bond areas, and the second areas may be smaller than the first areas.

In a twenty-fifth embodiment, the bonds which are spaced apart in the longitudinal direction a distance less than the un-tensioned diameter of the elastomeric strand, of the material of the twenty-third embodiment, may be polygons, and the bonds which are spaced apart in the longitudinal direction a distance greater than the un-tensioned diameter of the elastomeric strand, of the material of the twenty-third embodiment, may be round.

In a twenty-seventh embodiment, the bonds of at least one bond pair of the second series of opposing bond pairs which define a portion of the second un-bonded channel, of the material of any of the twenty-second through twenty-sixth embodiments, may be spaced apart in the longitudinal direction a distance less than an un-tensioned diameter of the elastomeric strand.

In a twenty-seventh embodiment, the bonds of at least one bond pair of the second series of opposing bond pairs which define a portion of the second un-bonded channel, of the material of any of the twenty-second through twenty-sixth embodiments, may be spaced apart in the longitudinal direction a distance greater than the un-tensioned diameter of the elastomeric strand.

In a twenty-eighth embodiment, the second portion of the elastomeric strand of the material of the twenty-seventh embodiment, which is disposed within the second un-bonded channel, may not pass between any bond pairs of the second series of opposing bond pairs which are spaced apart in the longitudinal direction a distance less than the un-tensioned diameter of the elastomeric strand.

In a twenty-ninth embodiment, the first series of opposing bond pairs, of the material of any of the twenty-first through twenty-eighth embodiments, may not be adjacent to the second series of opposing bond pairs.

In a thirtieth embodiment, the material of any of the twenty-first through twenty-ninth embodiments may further comprise a third series of opposing bond pairs extending in the lateral direction and spaced longitudinally from the first series of opposing bond pairs and the second series of opposing bond pairs, the third series of opposing bond pairs defining a third un-bonded channel extending between the third series of opposing bond pairs, and a third portion of the of the elastomeric strand may be disposed within the third un-bonded channel.

In a thirty-first embodiment, a third portion of the elastomeric strand of any of the twenty-first through thirtieth embodiments may be disposed within the first un-bonded channel, the second portion being disposed between the first portion and the third portion.

In a thirty-second embodiment, an elasticated material extending in a lateral direction and a longitudinal direction may comprise a first web of material, a second web of material bonded to the first web of material by a plurality of bonds, at least some of the plurality of bonds forming bond pairs, and an elastomeric strand extending in the lateral direction and disposed between the first web of material and the second web of material. The elastomeric strand may form an arcuate shape, and the elastomeric strand may extend between a plurality of the bond pairs, at least some of the plurality of the bond pairs having bonds which are separated by a longitudinal distance that is less than an un-tensioned diameter of the elastomeric strand.

In a thirty-third embodiment, at least some of the plurality of bond pairs of the thirty-second embodiment through which the elastomeric strand extends may have bonds which are separated by a longitudinal distance that is greater than an un-tensioned diameter of the elastomeric strand.

In a thirty-fourth embodiment, the bonds of the thirty-third embodiment which are separated by a longitudinal distance that is less than an un-tensioned diameter of the elastomeric strand may have first bond areas, and the bonds which are spaced apart in the longitudinal direction a distance greater than the un-tensioned diameter of the elastomeric strand may have second bond areas which are less than the first bond areas.

In a thirty-fifth embodiment, the bonds of any of the thirty-third and thirty-fourth embodiments which are spaced apart in the longitudinal direction a distance less than the un-tensioned diameter of the elastomeric strand may be polygons, and the bonds which are spaced apart in the longitudinal direction a distance greater than the un-tensioned diameter of the elastomeric strand may be round.

In a thirty-sixth embodiment, the elastomeric strand of any of the thirty-third through thirty-fifth embodiments may extend through the bonds which are spaced apart in the longitudinal direction a distance less than the un-tensioned diameter of the elastomeric strand in a straight path, and the elastomeric strand may extend through the bonds which are spaced apart in the longitudinal direction a distance greater than the un-tensioned diameter of the elastomeric strand in an arcuate path.

What is claimed is:

1. A method for forming an elasticated material, the method comprising:
    advancing a first continuous substrate material having an upper surface and a lower surface in a machine direction;
    advancing a second continuous substrate material having an upper surface and a lower surface in the machine direction;
    advancing an elastomeric strand in a stretched state in the machine direction, wherein the elastomeric strand is positioned between the lower surface of the first continuous substrate material and the upper surface of the second continuous substrate material;
    advancing the first continuous substrate material and the second continuous substrate material with the elastomeric strand positioned therebetween to a bonding apparatus, wherein the bonding apparatus comprises:
        a first bonding element,
        a second bonding element disposed proximate the first bonding element and forming a bonding nip with the first bonding element, and
        a guide element disposed proximate the second bonding element and forming a guide nip with the second bonding element;
    oscillating the elastomeric strand in a cross-machine direction;
    advancing the second continuous substrate and the elastomeric strand through the guide nip so that the second continuous substrate and the elastomeric strand contact the second bonding element prior to the bonding nip; and
    advancing the first continuous substrate material, the second continuous substrate material, and the elastomeric strand through the bonding nip and bonding the first continuous substrate material to the second continuous substrate material with the elastomeric strand disposed therebetween with at least a first bond and a second bond,
    wherein the first bond and the second bond are disposed on opposite sides of the elastomeric strand and spaced apart a distance less than an un-tensioned diameter of the elastomeric strand,
    wherein the second bonding element is a roll having an outer edge comprising a circumference, and wherein the guide nip is disposed such that a distance between the bonding nip and the guide nip, along the outer edge of the second bonding element, is between about 5% and about 75% of the circumference, and
    wherein the first bond and the second bond are located along a portion of the elastomeric strand which extends in an arcuate manner.

2. The method of claim 1, wherein the guide nip is disposed such that a distance between the bonding nip and the guide nip, along the outer edge of the second bonding element, is between about 15% and about 50% of the circumference.

3. The method of claim 1, further comprising advancing the first continuous substrate material through the guide nip along with the second continuous substrate material and the first continuous substrate material.

4. The method of claim 1, wherein bonding the first continuous substrate material to the second continuous substrate material with the elastomeric strand disposed therebetween further comprises:
    forming a third bond and a fourth bond disposed on opposite sides of the elastomeric strand,
    wherein the third bond and the fourth bond are spaced apart a distance less than an un-tensioned diameter of the elastomeric strand, and
    wherein the third bond and the fourth bond are located along a portion of the elastomeric strand which extends in a straight manner.

5. The method of claim 1, wherein method does not include a step of applying adhesive between the first continuous substrate material and the second continuous substrate material.

6. The method of claim 1, wherein at least one of the first bonding element and the second bonding element comprise rolls.

7. The method of claim 1, wherein the guide nip is disposed such that a distance between the bonding nip and the guide nip, along the outer edge of the second bonding element, is between about 20% and about 30% of the circumference.

* * * * *